(12) United States Patent
Bouix-Peter et al.

(10) Patent No.: US 8,962,846 B2
(45) Date of Patent: *Feb. 24, 2015

(54) MELANOCORTIN RECEPTOR ANTAGONIST COMPOUNDS, PROCESS FOR PREPARING THEM AND USE THEREOF IN HUMAN MEDICINE AND COSMETICS

(75) Inventors: Claire Bouix-Peter, Vallauris (FR); Isabelle Carlavan, Grasse (FR); Catherine Soulet, Antibes (FR); Veronique Parnet, Le Cannet (FR); Johannes Voegel, Chateauneuf/Grasse (FR)

(73) Assignee: Galderma Research & Development, Biot (FR)

( * ) Notice: Subject to any disclaimer, the term of this patent is extended or adjusted under 35 U.S.C. 154(b) by 666 days.

This patent is subject to a terminal disclaimer.

(21) Appl. No.: 13/126,221

(22) PCT Filed: Nov. 4, 2009

(86) PCT No.: PCT/EP2009/064651
§ 371 (c)(1),
(2), (4) Date: Jul. 29, 2011

(87) PCT Pub. No.: WO2010/052256
PCT Pub. Date: May 14, 2010

(65) Prior Publication Data
US 2011/0281913 A1  Nov. 17, 2011

Related U.S. Application Data

(60) Provisional application No. 61/111,188, filed on Nov. 4, 2008.

(30) Foreign Application Priority Data

Nov. 4, 2008 (FR) ...................... 08 57499

(51) Int. Cl.
C07D 401/00 (2006.01)
A61K 31/445 (2006.01)
C07D 401/12 (2006.01)
C07D 403/12 (2006.01)

(52) U.S. Cl.
CPC ............ C07D 401/12 (2013.01); C07D 403/12 (2013.01)
USPC .......................................... 546/208; 514/326

(58) Field of Classification Search
CPC ....................................................... C07D 401/06
USPC .......................................... 546/208; 514/326
See application file for complete search history.

(56) References Cited

PUBLICATIONS

Heroin et al Journal of Medicinal Chemistry 2003, 46, 1123-1126.*

* cited by examiner

*Primary Examiner* — John Mabry
(74) *Attorney, Agent, or Firm* — Denton US LLP

(57) ABSTRACT

Melanocortin receptor antagonist compounds, processes for preparing them and uses thereof in human medicine and cosmetics are described.

Melanocortin receptor antagonist compounds corresponding to the general formula (I):

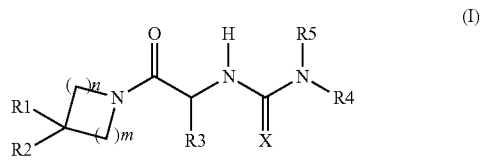

compositions containing them, and processes for their preparation and their use in pharmaceutical or cosmetic compositions are also described.

18 Claims, 11 Drawing Sheets

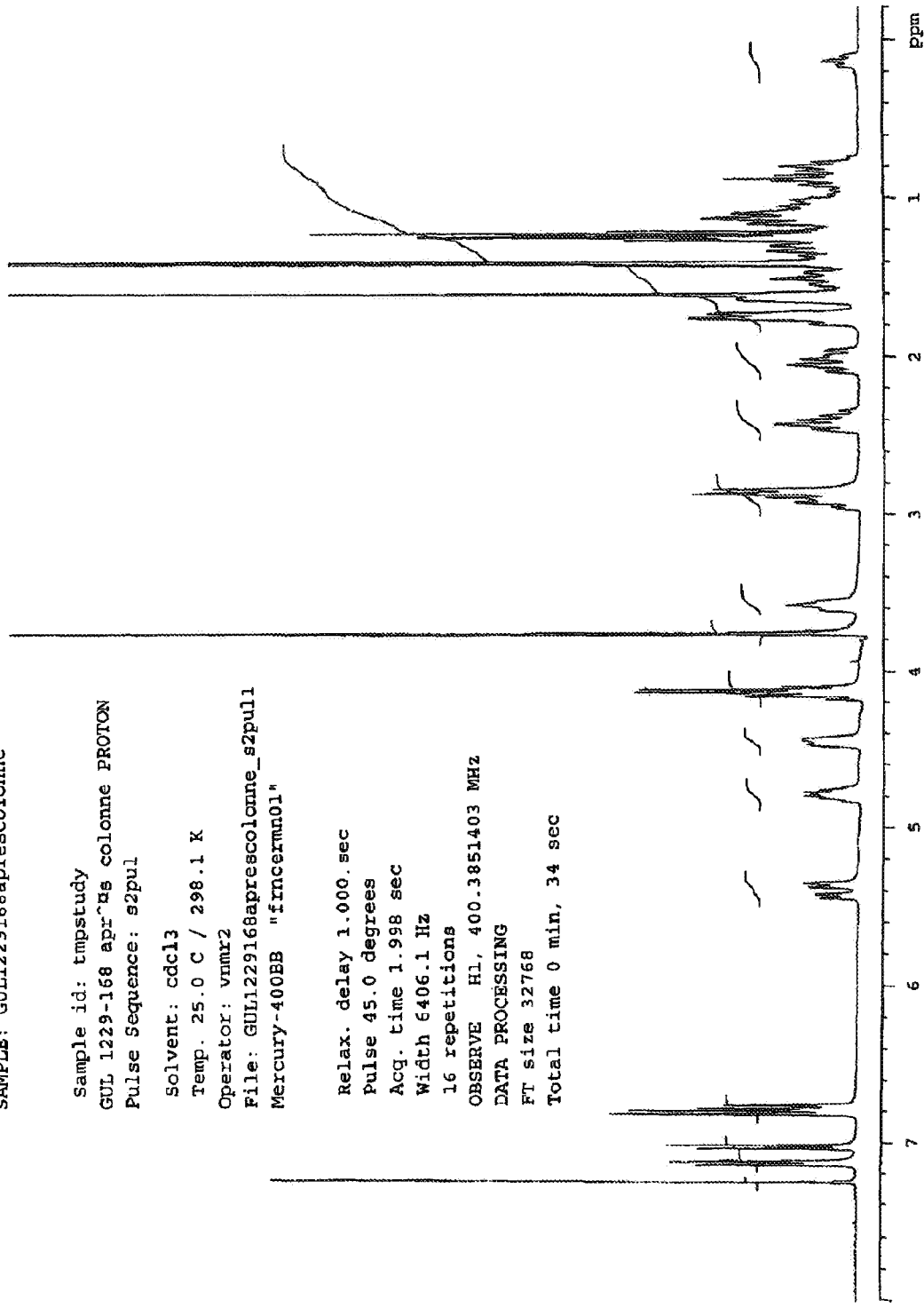

MELANOCORTIN RECEPTOR ANTAGONIST COMPOUNDS, PROCESS FOR PREPARING THEM AND USE THEREOF IN HUMAN MEDICINE AND COSMETICS

This application is the United States national phase of PCT/EP2009/064651, filed Nov. 4, 2009, and designating the United States (published in the English language on May 14, 2010, as WO 2010/052256 A1; the title and abstract were also published in English), which claims benefit of U.S. Provisional Application No. 61/111,188, filed Nov. 4, 2008, and also claims priority under 35 U.S.C. §119 of FR 0857499, filed Nov. 4, 2008, each hereby expressly incorporated by reference in its entirety and each assigned to the assignee hereof.

The invention relates to novel compounds as antagonist products of one or more melanocortin receptors. The invention also relates to a process for preparing them and to their therapeutic use.

Melanocortins form the family of regulatory peptides that are synthesized via a post-translational process of the hormone propiomelanocortin (POMC—131 amino acids long). POMC leads to the production of three classes of hormone: melanocortins, the hormone adrenocorticotropin and various endorphins, for instance lignotropin (Cone, et al., Recent Prog. Horm. Res. 51: 287-317, (1996); Cone et al., Ann. N.Y. Acad. Sc., 31: 342-363, (1993).

Melanocortin receptors (MCRs) form part of the superfamily of GPCRs with seven transmembrane domains. To date, five subtypes of receptor, MC1-5R, have been identified in mammals. An endogenous group of peptides binds to MCRs with agonist or antagonist effects, for instance the melanocyte-stimulating hormones (MSH), adrenocorticotropic hormone (ACTH), and the Agouti proteins and derivatives thereof. However, an exception is the MC2R receptor, which binds only with ACTH (Major pharmacological distinction of the ACTH receptor from other melanocortin receptors, Schioth et al., Life Sciences (1996), 59(10), 797-801).

MCRs have varied physiological roles. MC1R regulates the formation of melanin in the skin, and has a role in regulating the immune system. MC2R regulates the production of corticosteroids in the adrenal glands. The receptors MC3R and MC4R play a role in controlling food intake and sexual behaviour. MC5R is involved in regulating the exocrine glands (Wikberg, Jarl E. S., Melanocortin receptors: perspectives for novel drugs. European Journal of Pharmacology (1999), 375(1-3), 295-310. Wikberg, Jarl E. S., Melanocortin receptors: new opportunities in drug discovery. Expert Opinion on Therapeutic Patents (2001), 11(1), 61-76).

The potential use of MCRs as targets for medicaments for treating major pathologies such as obesity, diabetes, inflammatory conditions and sexual dysfunction raises the need for compounds that show high specificity towards a particular subtype. However, the modelling of selective medicaments, for slightly different receptor subtypes, is a difficult task that would be simplified in the light of detailed knowledge regarding the determinants of the ligand-receptor interaction.

The Applicant has now found, surprisingly and unexpectedly, that certain compounds of general formula (I), which is the subject of the present invention, are selective MC4-R antagonists.

The pathologies described as being associated with dysfunction of the MC4 receptor concern weight regulation (homeostasis), sexual dysfunctions, depression and anxiety (Chaki et al, Current Topics in Medicinal Chemistry, 2007, 1145-1151), and bones (Cart overexpression is the only identifiable cause of high bone mass in melanocortin 4 receptor deficiency, Endocrinology, 2006 July; 147(7):3196-202).

Mention may be made in particular of disorders associated with weight loss (including involuntary weight loss) such as anorexia. Mention may also be made of cachexia (The role of central melanocortins in cachexia, Contemporary Endocrinology: Energy Metabolism and Obesity: Research and Clinical Applications, pp. 59-68) and related indications such as sarcopenia (Cofemer 2008 by P. Dehail), catabolic diseases, and cancer- or HIV-related cachexia. Specifically, cachexia is defined hereinbelow as a profound weakening of the body (weight loss, muscular atrophy, etc.), associated with very substantial denutrition. Cachexia is not a disease in itself, but the symptom of another. It may arise from an anorexia (even in the case of a person whose weight loss is not voluntary), a cancer (cancer-related cachexia, produced by substances secreted by the tumour, cachexins), chronic diseases (COPD, cardiac insufficiency, hepatic insufficiency, renal insufficiency) or even certain infectious diseases (for example tuberculosis and AIDS, or certain autoimmune diseases).

Patents WO 02/070 511, WO 02/079 146 and WO 02/069 905 claim the use of compounds as modulators of melanocortin receptors, more particularly MC1-R and MC4-R.

Chen describes the recent advances in the discovery of non-peptide ligands of the MC4-R receptor (Progress in Medicinal Chemistry, Vol. 45, p. 111-167).

Chen et al. describe the use of selective MC4-R antagonists as a potential treatment for cachexia (Current Topics in Medicinal Chemistry, 2007, 1131-1136).

Pontillo et al. describe substituted phenylpiperazine compounds as selective antagonists of the MC4 receptors, administration of which makes it possible to increase food intake in mice (A potent and selective non-peptide antagonist of the melanocortin-4 receptor induces food intake in satiated mice—Bioorganic & Medicinal Chemistry Letters 15 (2005) 2541-46).

Vos et al. describe the identification of a novel series of MC4-R antagonists (Bioorganic & Medicinal Chemistry Letters 16 (2006) 2302-2305).

Chen et al. describe the identification of novel selective MC4-R antagonists derived from phenylpiperazines and from pyridinylpiperazines (Journal of Medicinal Chemistry, 2007, 6356-6366).

Now, the Applicant has demonstrated, unexpectedly, that certain compounds of formula (I) as described hereinbelow, have melanocortin receptor antagonist properties, and in particular for the receptors of the MC4 type.

Thus, the present invention relates to compounds of general formula (I) below:

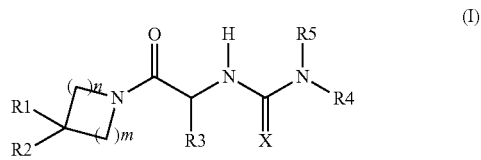

in which:
R1 represents a hydrogen atom, an aryl, a substituted aryl, an alkyl, a cycloalkyl or a cycloalkylalkyl,
R2 represents a hydrogen atom, a hydroxyl, a lower alkyl, a substituted lower alkyl, a higher alkyl, a substituted higher alkyl, a cycloalkyl, a cycloalkylalkyl, a lower alkoxy, a substituted lower alkoxy, a higher alkoxy, a substituted higher alkoxy, a cycloalkylalkoxy, an acyloxy, an acyl, an alkoxycarbonyl, a carboxamide, a carboxylic acid, a cyano, or an amino disubstituted with an acyl and an aryl or alkyl, R3 represents an aralkyl or a substituted aralkyl, R4 represents a heteroaralkyl or a substituted heteroaralkyl, R5 represents a hydrogen atom or an alkyl, X represents an oxygen atom or a sulfur atom, n, m may be equal to 1 or 2;

and also the corresponding salts and enantiomers and are characterized in that they have antagonist activity with respect to the MC4-R receptor. In particular, their antagonist activity with respect to the MC4-R receptor, EC50, is less than or equal to 60 nM.

BRIEF DESCRIPTION OF THE DRAWINGS:

FIG. 3a depicts $^1$H NMR/CDCl$_3$ results for the product of Example 4-3, ethyl 1-[(R)-2-tert-butoxycarbonylamino-3-(4-methoxyphenyl)propionyl]-4-cyclohexylpiperidine-4-carboxylate (mixture of conformers).

Figure 1:
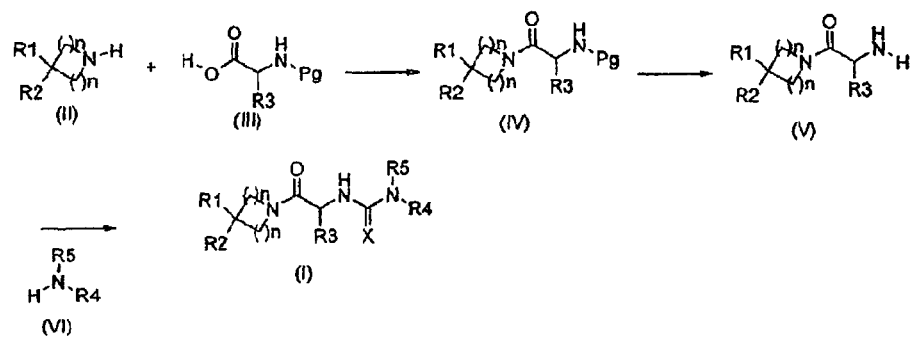
FIG. 1 is a depiction of a reaction scheme for the preparation of the compounds of formula (I).

Among the addition salts of the compounds of general formula (I) with a pharmaceutically acceptable acid, mention may be made preferably of the salts with an organic acid or with a mineral acid.

The suitable mineral acids are, for example, hydrohalic acids, for instance hydrochloric acid or hydrobromic acid, sulfuric acid and nitric acid.

The suitable organic acids are, for example, picric acid, methanesulfonic acid, ethanesulfonic acid, para-toluenesulfonic acid, oxalic acid and tartaric acid.

The compounds of general formula (I) may also exist in the form of hydrates or solvates with water or with a solvent.

The suitable solvents for forming solvates or hydrates are, for example, alcohols, for instance ethanol or isopropanol, or water.

According to the present invention, the term "aryl" denotes an unsubstituted phenyl or naphthyl.

According to the present invention, the term "substituted aryl" denotes a phenyl or a naphthyl substituted with one or more groups of atoms chosen from an alkyl, an alkoxy, a halogen, a hydroxyl, a cyano, a trifluoromethyl and a nitro.

According to the present invention, the term "cycloalkyl" denotes a saturated cyclic hydrocarbon-based chain containing from 3 to 7 carbon atoms.

According to the present invention, the term "hydroxyl" means the OH group.

According to the present invention, the term "amino" means the NH$_2$ group.

According to the present invention, the term "cyano" denotes the CN group.

According to the present invention, the term "carboxylic acid" denotes the CO$_2$H group.

According to the present invention, the term "acyl" denotes a formyl or a carbonyl substituted with an alkyl, a cycloalkyl or a cycloalkylalkyl.

According to the present invention, the term "alkyl" denotes a substituted or unsubstituted lower alkyl or higher alkyl.

According to the present invention, the term "lower alkyl" denotes a linear or branched, saturated or unsaturated hydrocarbon-based chain containing from 1 to 4 carbon atoms or an unsaturated chain containing from 2 to 4 carbon atoms and especially, for example, methyl, ethyl, propyl, isopropyl and butyl.

According to the present invention, the term "substituted lower alkyl" means a linear or branched, saturated or unsaturated hydrocarbon-based chain containing from 1 to 4 carbon atoms and substituted with one or more halogen atoms or with a hydroxyl, or an unsaturated hydrocarbon-based chain containing from 2 to 4 carbon atoms and substituted with one or more halogen atoms or with a hydroxyl.

According to the present invention, the term "higher alkyl" denotes a linear or branched, saturated or unsaturated hydrocarbon-based chain containing from 5 to 10 carbon atoms.

According to the present invention, the term "substituted higher alkyl" denotes a linear or branched, saturated or unsaturated hydrocarbon-based chain containing from 5 to 10 carbon atoms and substituted with one or more halogen atoms or with a hydroxyl.

According to the present invention, the term "halogen atom" means chlorine, fluorine, iodine and bromine atoms.

According to the present invention, the term "cycloalkylalkyl" denotes an alkyl substituted with a cycloalkyl.

According to the present invention, the term "lower alkoxy" denotes an oxygen atom substituted with a lower alkyl.

According to the present invention, the term "substituted lower alkoxy" denotes an oxygen atom substituted with a substituted lower alkyl.

According to the present invention, the term "higher alkoxy" denotes an oxygen atom substituted with a higher alkyl.

According to the present invention, the term "substituted higher alkoxy" denotes an oxygen atom substituted with a substituted higher alkyl.

According to the present invention, the term "cycloalkylalkoxy" denotes an oxygen atom substituted with a cycloalkylalkyl.

According to the present invention, the term "acyloxy" denotes an oxygen atom substituted with an acyl.

According to the present invention, the term "alkoxycarbonyl" denotes a carbonyl substituted with an alkoxy, cycloalkoxy or a cycloalkylalkoxy.

According to the present invention, the term "carboxamide" denotes a carbonyl substituted with a monoalkylamino or a dialkylamino.

According to the present invention, the term "aralkyl" denotes an alkyl substituted with an aryl.

According to the present invention, the term "substituted aralkyl" denotes an alkyl substituted with a substituted aryl.

According to the present invention, the term "heterocycle" denotes a saturated or unsaturated, cyclic or bicyclic hydrocarbon-based chain, comprising one or more heteroatoms chosen from O, S and N.

According to the present invention, the term "substituted heterocycle" denotes a saturated or unsaturated, cyclic or bicyclic hydrocarbon-based chain, comprising one or more heteroatoms chosen from O, S and N substituted with one or more alkyl groups.

According to the present invention, the term "heteroaryl" denotes an aromatic heterocycle.

According to the present invention, the term "substituted heteroaryl" denotes an aromatic heterocycle substituted with one or more alkyl groups.

According to the present invention, the term "heteroaralkyl" denotes an alkyl substituted with a heteroaryl.

According to the present invention, the term "substituted heteroaralkyl" denotes an alkyl substituted with a substituted heteroaryl.

Among the compounds of general formula (I) included in the context of the present invention, mention may be made especially of the following:

tert-Butyl 4-cyclohexyl-1-[2-{3-[2-(1H-imidazol-4-yl)ethyl]ureido}-3-(4-methoxyphenyl)-propionyl]piperidine-4-carboxylamide 1-[(R)-2-(4-Butyryl-4-cyclohexylpiperidin-1-yl)-1-(4-methoxybenzyl)-2-oxoethyl]-3-[2-(1-methyl-1H-imidazol-4-yl)ethyl]urea 1-[(R)-2-(4-Butyryl-4-cyclohexylpiperidin-1-yl)-1-(4-methoxybenzyl)-2-oxoethyl]-3-[2-(1H-[1,2,3]triazol-4-yl)ethyl]urea Ethyl 4-cyclohexyl-1-[(R)-2-{3-[3-(3H-imidazol-4-yl)propyl]ureido}-3-(4-methoxy-phenyl)propionyl]piperidine-4-carboxylate Ethyl 4-cyclohexyl-1-((R)-3-(3,4-dichlorophenyl)-2-{3-[2-(1H-imidazol-4-yl)ethyl]-ureido}propionyl)piperidine-4-carboxylate Ethyl 4-cyclohexyl-1-((R)-3-(3,4-dichlorophenyl)-2-{3-[2-(3-methyl-3H-imidazol-4-yl)-ethyl]ureido}propionyl)piperidine-4-carboxylate Ethyl 4-cyclohexyl-1-[(R)-2-{3-[3-(1H-imidazol-4-yl)propyl]thioureido}-3-(4-methoxy-phenyl)propionyl]piperidine-4-carboxylate Ethyl 4-cyclohexyl-1-((R)-3-(4-methoxyphenyl)-2-{3-[2-(1-methyl-1H-imidazol-4-yl)-ethyl]thioureido}propionyl)piperidine-4-carboxylate Ethyl 4-cyclohexyl-1-((R)-3-(2,4-dichlorophenyl)-2-{3-[2-(1H-imidazol-4-yl)ethyl]-ureido}propionyl)piperidine-4-carboxylate Ethyl 4-cyclohexyl-1-[(R)-2-{3-[5-(1H-imidazol-4-yl)pentyl]ureido}-3-(4-methoxy-phenyl)propionyl]piperidine-4-carboxylate 4-Cyclohexyl-1-(3-(4-methoxyphenyl)-2-{3-[(R)-2-(1-methyl-1H-imidazol-4-yl)ethyl]-ureido}propionyl)piperidine-4-tert-butylcarbamoyl 4-Cyclohexyl-1-(3-(4-methoxyphenyl)-2-{3-[(R)-2-(1H-[1,2,3]triazol-4-yl)ethyl]ureido}-propionyl)piperidine-4-tert-butylcarbamoyl 4-Cyclohexyl-1-[(R)-2-{3-[3-(1H-imidazol-4-yl)propyl]ureido}-3-(4-methoxyphenyl)-propionyl]piperidine-4-tert-butylcarbamoyl 4-Cyclohexyl-1-[(R)-2-{3-[5-(1H-imidazol-4-yl)pentyl]ureido}-3-(4-methoxyphenyl)-propionyl]piperidine-4-tert-butylcarbamoyl 4-Cyclohexyl-1-((R)-3-(4-methoxyphenyl)-2-{3-[2-(1-methyl-1H-imidazol-4-yl)ethyl]-thioureido}propionyl)piperidine-4-tert-butylcarbamoyl 4-Cyclohexyl-1-[(R)-2-{3-[3-(1H-imidazol-4-yl)propyl]thioureido}-3-(4-methoxyphenyl)-propionyl]piperidine-4-tert-butylcarbamoyl 1-[(R)-2-(4-Butyryl-4-cyclohexylpiperidin-1-yl)-1-(4-methoxybenzyl)-2-oxoethyl]-3-[2-(1-methyl-1H-imidazol-4-yl)ethyl]thiourea 1-[(R)-2-(4-Butyryl-4-cyclohexylpiperidin-1-yl)-1-(4-methoxybenzyl)-2-oxoethyl]-3-[2-(1H-[1,2,3]triazol-4-yl)ethyl]thiourea Ethyl 4-cyclohexyl-1-((R)-3-(3,4-dichlorophenyl)-2-{3-[2-(1-methyl-1H-imidazol-4-yl)-ethyl]ureido}propionyl)piperidine-4-carboxylate Ethyl 4-cyclohexyl-1-((R)-3-(3,4-dichlorophenyl)-2-{3-[5-(1H-imidazol-4-yl)pentyl]-ureido}propionyl)piperidine-4-carboxylate Ethyl 4-cyclohexyl-1-((R)-3-(2,4-dichlorophenyl)-2-{3-[2-(1-methyl-1H-imidazol-4-yl)-ethyl]ureido}propionyl)piperidine-4-carboxylate Ethyl 4-cyclohexyl-1-((R)-3-(2,4-dichlorophenyl)-2-{3-[2-(3-methyl-3H-imidazol-4-yl)-ethyl]ureido}propionyl)piperidine-4-carboxylate Ethyl 4-cyclohexyl-1-((R)-3-(2,4-dichlorophenyl)-2-{3-[5-(1H-imidazol-4-yl)pentyl]-ureido}propionyl)piperidine-4-carboxylate 1-[(R)-2-(4-Cyclohexyl-4-propoxypiperidin-1-yl)-1-(4-methoxybenzyl)-2-oxoethyl]-3-[2-(1-methyl-1H-imidazol-4-yl)ethyl]urea 1-[(R)-2-(4-Cyclohexyl-4-propoxypiperidin-1-yl)-1-(4-methoxybenzyl)-2-oxoethyl]-3-[2-(1H-[1,2,3]triazol-4-yl)ethyl]urea 1-[(R)-2-(4-Cyclohexyl-4-propoxypiperidin-1-yl)-1-(4-methoxybenzyl)-2-oxoethyl]-3-[3-(1H-imidazol-4-yl)propyl]urea 1-[(R)-2-(4-Cyclohexyl-4-propoxypiperidin-1-yl)-1-(4-methoxybenzyl)-2-oxoethyl]-3-[5-(1H-imidazol-4-yl)pentyl]urea 1-[(R)-2-(4-Cyclohexyl-4-propoxypiperidin-1-yl)-1-(4-methoxybenzyl)-2-oxoethyl]-3-[2-(1-methyl-1H-imidazol-4-yl)ethyl]thiourea 1-[2-(4-Cyclohexyl-4-propoxypiperidin-1-yl)-1-(4-methoxybenzyl)-2-oxoethyl]-3-[3-(1H-imidazol-4-yl)propyl]thiourea 1-[(R)-2-(4-Butyryl-4-cyclohexylpiperidin-1-yl)-1-(4-chlorobenzyl)-2-oxoethyl]-3-[2-(1-methyl-1H-imidazol-4-yl)ethyl]urea 1-[(R)-2-(4-Butyryl-4-cyclohexylpiperidin-1-yl)-1-(4-chlorobenzyl)-2-oxoethyl]-3-[2-(1H-[1,2,3]triazol-4-yl)ethyl]urea 1-[(R)-2-(4-Butyryl-4-cyclohexylpiperidin-1-yl)-1-(4-chlorobenzyl)-2-oxoethyl]-3-[3-(1H-imidazol-4-yl)propyl]urea 1-[(R)-2-(4-Butyryl-4-cyclohexylpiperidin-1-yl)-1-(4-chlorobenzyl)-2-oxoethyl]-3-[5-(1H-imidazol-4-yl)pentyl]urea 1-[(R)-2-(4-Butyryl-4-cyclohexylpiperidin-1-yl)-1-(4-chlorobenzyl)-2-oxoethyl]-3-[2-(1-methyl-1H-imidazol-4-yl)ethyl]thiourea 1-[(R)-2-(4-Butyryl-4-cyclohexylpiperidin-1-yl)-1-(4-chlorobenzyl)-2-oxoethyl]-3-[3-(1H-imidazol-4-yl)propyl]thiourea 1-[(R)-2-(4-Butyryl-4-cyclohexylpiperidin-1-yl)-1-(2,4-dichlorobenzyl)-2-oxoethyl]-3-(1H-imidazol-4-yl)methyl)urea 1-[(R)-2-(4-Butyryl-4-cyclohexylpiperidin-1-yl)-1-(4-fluorobenzyl)-2-oxoethyl]-3-[2-(1-methyl-1H-imidazol-4-yl)ethyl]urea 1-[(R)-2-(4-Butyryl-4-cyclohexylpiperidin-1-yl)-1-(4-fluorobenzyl)-2-oxoethyl]-3-[2-(1H-[1,2,3]triazol-4-yl)ethyl]urea 1-[(R)-2-(4-Butyryl-4-cyclohexylpiperidin-1-yl)-1-(4-fluorobenzyl)-2-oxoethyl]-3-[3-(1H-imidazol-4-yl)propyl]urea 1-[(R)-2-(4-Butyryl-4-cyclohexylpiperidin-1-yl)-1-(4-fluorobenzyl)-2-oxoethyl]-3-[5-(1H-imidazol-4-yl)pentyl]urea 1-[(R)-2-(4-Butyryl-4-cyclohexylpiperidin-1-yl)-1-(4-fluorobenzyl)-2-oxoethyl]-3-[2-(1-methyl-1H-imidazol-4-yl)ethyl]thiourea 1-[(R)-2-(4-Butyryl-4-cyclohexylpiperidin-1-yl)-1-(4-fluorobenzyl)-2-oxoethyl]-3-[3-(1H-imidazol-4-yl))propyl]thiourea and also the corresponding salts and enantiomers.

The compounds of general formula (I) are prepared according to the general reaction schemes presented in FIG. 1.

Using reaction scheme 1 (FIG. 1):

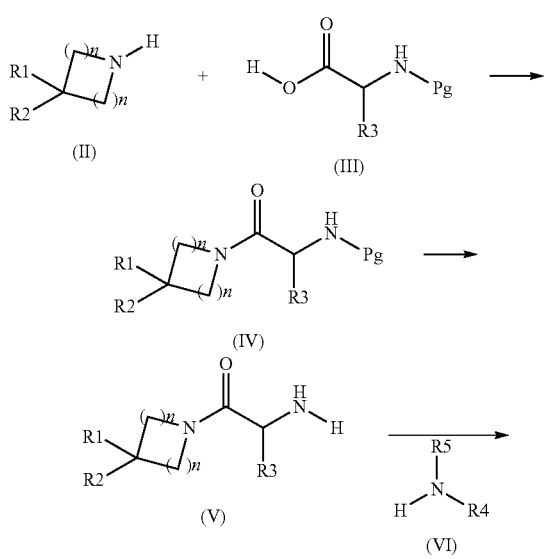

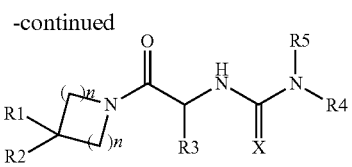

(I)

According to scheme 1, the compounds of formula (IV) may be prepared by coupling between the intermediates of formula (II) and an amino acid of formula (III) whose amine function is protected with a protecting group Pg (for example a Boc, CBz or Fmoc group), under standard peptide coupling conditions (Han, S., Kim, Y. Tetrahedron, 2004, 60, 2447-2467; Albericio, F. Current Opinion in Chemical Biology, 2004, 8, 211-221; Humphrey, J., Chamberlin, R. Chem. Rev., 1997, 97, 2243-2266), using, for example, as coupling agent 1-(3-dimethylaminopropyl)-3-ethylcarbodiimide hydrochloride, hydroxybenzotriazole or TBTU, and as base triethylamine or diisopropylethylamine, in a solvent such as dichloromethane or dimethylformamide.

The amino acids of general formula (IV) are commercially available or may be prepared via methods described in the literature (Williams, R. M., Synthesis of optically active α-amino acids, Pergamon Press, Oxford, 1989).

The compounds of formula (V) are obtained by deprotection of the amine function of the compounds of formula (IV), via methods chosen from those known to a person skilled in the art. They include, inter alia, the use of trifluoroacetic acid or hydrochloric acid in dichloromethane, or ethyl acetate, for example in the case of a protection with a Boc group, hydrogenation with the appropriate metal in tetrahydrofuran or methanol, for example in the case of a protection with a CBz group, and piperidine in acetonitrile, for example in the case of a protection with an Fmoc group.

In a final step, the compounds of formula (I) may be prepared by adding the amines of formula (VI) to isocyanates or isothiocyanates obtained from the compounds (V) in dichloromethane or dimethylformamide, for example. The isocyanates may be prepared from the amines (V) in the presence of phosgene, diphosgene or triphosgene, for example. The isothiocyanates may be prepared from the amines (V) in the presence of thiophosgene (Nowick J. S. et al., JOC (1996) 3929-3934), or bis(2-pyridyl) thionocarbonate (WO 2008/008 954), for example. The compounds of formula (I) may also be synthesized by adding the amines of formula (VI) to activated carbamates obtained from the amines (V) in dichloromethane or dimethylformamide, for example. The term "activated carbamate" means, for example, a para-nitrophenyl carbamate group (Igarashi, T., Synlett (2007) 1436), which may be obtained by adding para-nitrophenyl chloroformate to the amine (V) in the presence of a base, which may be, for example, triethylamine in dichloromethane or dimethylformamide.

The compounds of formula (II) are commercially available or may be prepared according to the methods described in the literature or known to those skilled in the art, adapted as a function of the nature of the substituents R1 and R2. Schemes 1 to 8 below show examples of preparation of the compounds of formula (II).

For example, when R2 contains an acyloxy or carboxamide chain, the preparation of the compound (II, n, m=2) may be performed according to scheme 1:

Scheme 1:

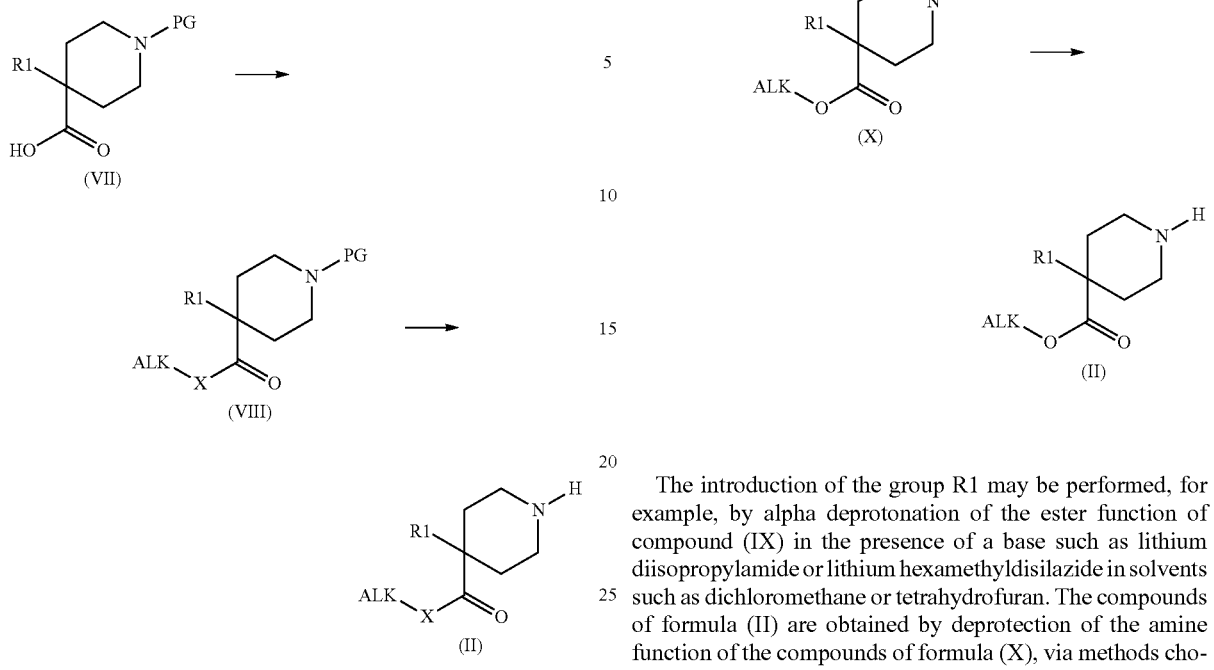

The compounds of formula (VIII) are obtained:
- when X is an oxygen, for example, by esterification of the carboxylic acid function of the compounds (VII) using the methods described in the literature, or
- when X is a nitrogen, for example by addition to an amine or to an acid chloride obtained from the carboxylic acid (VII) using methods chosen from those known to a person skilled in the art. It is especially possible to use oxalyl chloride or thionyl chloride in solvents such as dichloromethane or dimethylformamide.

The compounds of formula (II) are obtained by deprotection of the amine function of the compounds of formula (VIII), via methods chosen from those known to a person skilled in the art. They include, inter alia, the use of trifluoroacetic acid or hydrochloric acid in dichloromethane, or ethyl acetate, for example in the case of a protection with a Boc group, hydrogenation with the appropriate metal in tetrahydrofuran or methanol, for example in the case of a protection with a CBz group, and piperidine in acetonitrile, for example in the case of a protection with an Fmoc group.

For example, when R1 contains an alkyl, cycloalkyl or cycloalkylalkyl group and R2 contains an acyloxy chain, the preparation of the compound (II, n, m=2) may be performed according to scheme 2:

Scheme 2:

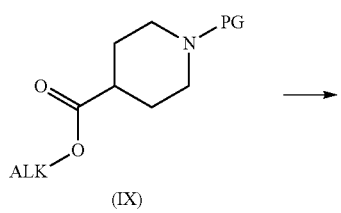

The introduction of the group R1 may be performed, for example, by alpha deprotonation of the ester function of compound (IX) in the presence of a base such as lithium diisopropylamide or lithium hexamethyldisilazide in solvents such as dichloromethane or tetrahydrofuran. The compounds of formula (II) are obtained by deprotection of the amine function of the compounds of formula (X), via methods chosen from those known to a person skilled in the art. They include, inter alia, the use of trifluoroacetic acid or hydrochloric acid in dichloromethane, or ethyl acetate, for example in the case of a protection with a Boc group, hydrogenation with the appropriate metal in tetrahydrofuran or methanol, for example in the case of a protection with a CBz group.

For example, when R2 contains an alkoxy or an alkoxycarbonyl chain, the preparation of the compound (II, n, m=1) may be performed according to scheme 3:

Scheme 3:

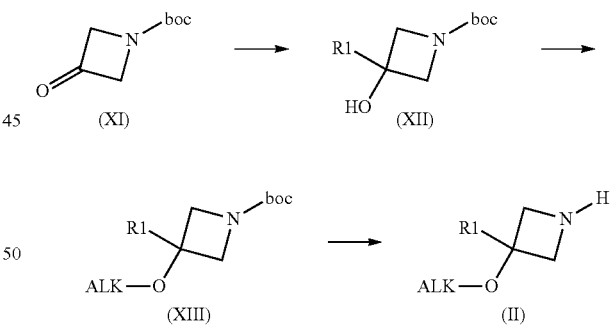

The compounds of formula (XII) are obtained, for example, by addition of a magnesium halide derived from R1 to the N-Boc-azetidinone (XI) followed by alkylation or acylation of the tertiary alcohol according to methods conventionally described in the literature, to lead to the compounds (XIII). The compounds of formula (II) are obtained by deprotection of the amine function of the compounds of formula (XIII), for example in the presence of trifluoroacetic acid or hydrochloric acid in dichloromethane or ethyl acetate.

For example, when R2 contains an acyl group, the preparation of the compound (II, n=m=1) may be performed according to scheme 4:

Scheme 4:

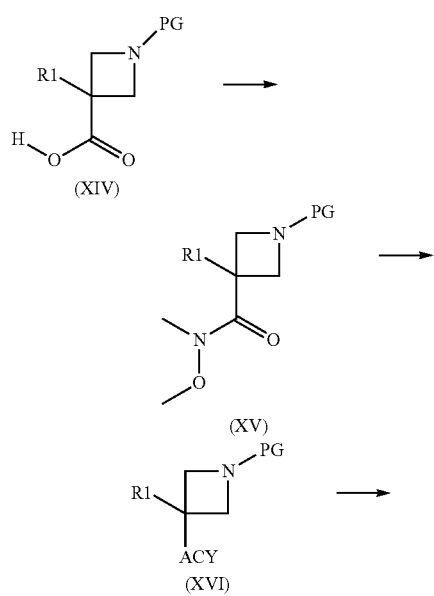

The compounds of formula (XV) may be obtained under peptide coupling conditions between compounds with a carboxylic acid (XIV) and the Weinreb amine, using, for example, as coupling agent, 1-(3-dimethylaminopropyl)-3-ethylcarbodiimide hydrochloride, hydroxybenzotriazole or TBTU, and, as base, triethylamine or diisopropylethylamine, in a solvent such as dichloromethane or dimethylformamide. The compounds of formula (XVI) are obtained, for example, by addition of a magnesium halide derived from R1 to the derivative of the Weinreb amide (XV). The compounds of formula (II) are obtained by deprotection of the amine function of the compounds of formula (X), via methods chosen from those known to a person skilled in the art. They include, inter alia, the use of trifluoroacetic acid or hydrochloric acid in dichloromethane, or ethyl acetate, for example in the case of a deprotection with a Boc group, hydrogenation with the appropriate metal in tetrahydrofuran or methanol, for example in the case of a protection with a CBz group.

For example, when R2 contains a disubstituted amine, the preparation of the compound (II, n=m=2) may be performed according to scheme 5:

Scheme 5:

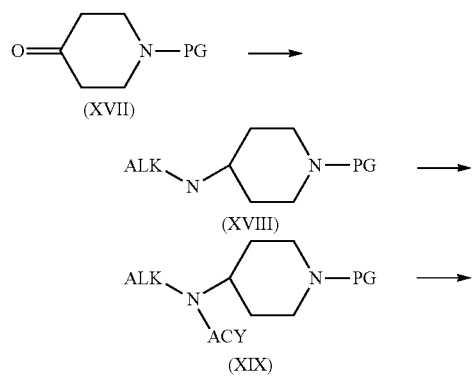

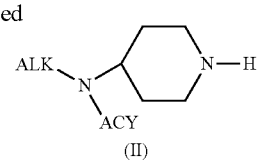

The compounds of formula (XVIII) may be obtained under reductive amination conditions between the commercially available ketone (XVII) and an amine in the presence of sodium borohydride or sodium cyanoborohydride, for example. The secondary amines (XVIII) may then be acylated in the presence of a base such as triethylamine and of an acid chloride, for example, to give the compounds (XIX). The compounds of formula (II) are obtained by deprotection of the amine function of the compounds of formula (VIII), via methods chosen from those known to a person skilled in the art. They include, inter alia, the use of trifluoroacetic acid or hydrochloric acid in dichloromethane or ethyl acetate, for example in the case of a protection with a Boc group, hydrogenation with the appropriate metal in tetrahydrofuran or methanol, for example in the case of a protection with a CBz group, and of piperidine in acetonitrile, for example in the case of a protection with an Fmoc group.

For example, when R1 contains a cyclohexyl and R2 contains an acyl group, the preparation of the compound (II, n=m=2) may be performed according to scheme 6:

Scheme 6:

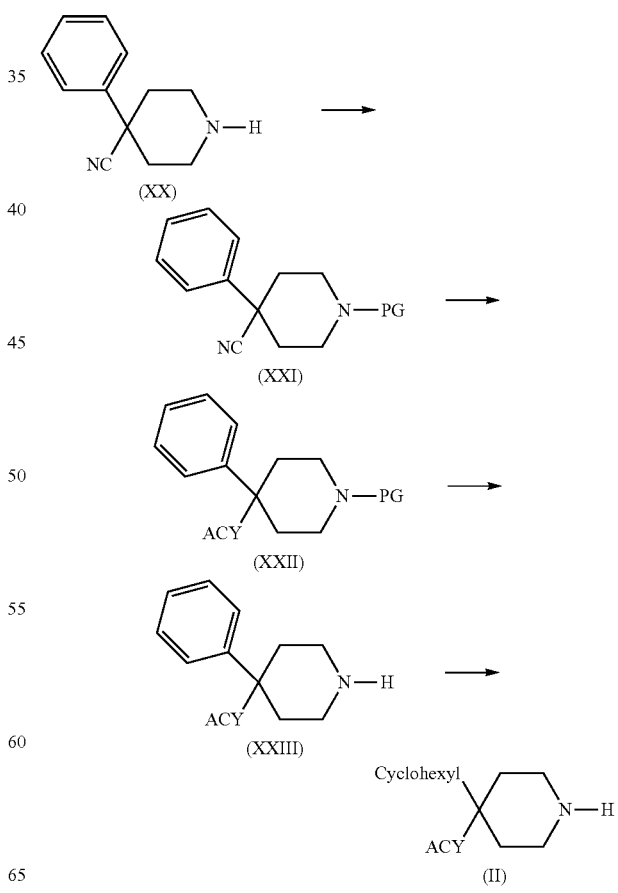

After protection of the commercially available amine (XX) with a tosylate group, for example by reacting tosyl chloride in the presence of a base such as triethylamine in dichloromethane, the compounds (XXI) are obtained. The compounds of formula (XXII) are obtained, for example, by addition of a magnesium halide derived from an alkyl in toluene to the nitrile function of the derivatives (XXI) followed by a hydrolysis in acidic medium of the intermediate imine, which may be hydrochloric acid. The compounds of formula (XXIII) are obtained by deprotection of the amine function in acidic medium, which may be sulfuric acid in the case of a tosylate group. The compounds (II) are obtained, for example, by hydrogenation of compound (X) in the presence of a catalyst, which may be rhodium on alumina or platinum oxide in dioxane, for example.

For example, when R1 is a cyclohexyl group and R2 is an alkoxy group, the preparation of the compound (II, n=m=2) may be performed according to scheme 7:

Scheme 7:

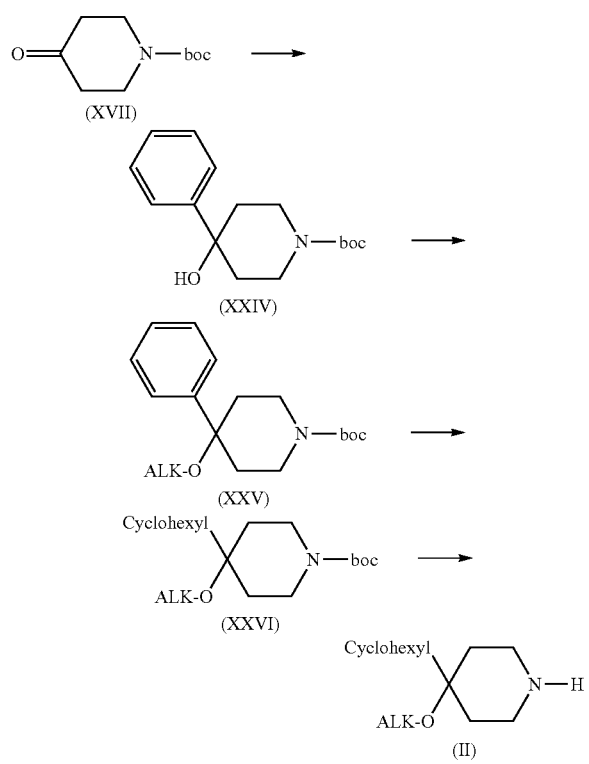

The compounds of formula (XXIV) are obtained, for example, by addition of a magnesium halide derived from a phenyl to the commercially available ketone (XVII) followed by alkylation of the tertiary alcohol according to methods conventionally described in the literature, to give the compounds (XXV). The compounds (XXVI) are obtained, for example, by hydrogenation of compound (XXV) in the presence of a catalyst, which may be rhodium on alumina or platinum oxide in dioxane, for example. The compounds of formula (II) are obtained by deprotection of the amine function of the compounds of formula (XXVI), for example in the presence of trifluoroacetic acid or hydrochloric acid in dichloromethane or ethyl acetate.

For example, when R1 is an aryl group and R2 contains an alkyl chain, the preparation of the compound (II, n=m=1) may be performed according to scheme 8:

Scheme 8:

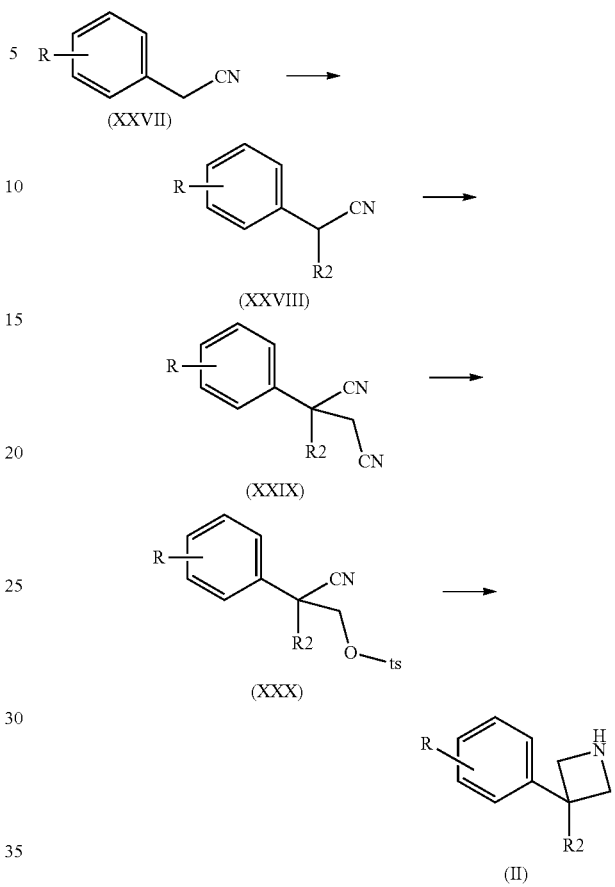

The compounds of formula (XXVIII) may be obtained, for example, by addition of a base, such as sodium hydride, in the presence of a halogenated derivative derived from R2 to the commercially available nitrile derivatives (XXVII). The primary alcohols (XXIX) may be synthesized from the nitrile derivatives (XXVIII) in the presence of a base, for example sodium hydride and paraformaldehyde. The primary alcohol function of the compounds (XXIX) may be converted into sulfonate in the presence of a base, which may be triethylamine, and of tosyl chloride, for example. The azetidine compounds (II) may be synthesized by intramolecular cyclization between an amine function obtained after reduction of the nitrile function, for example, in the presence of lithium aluminium hydride and the tosylate function.

The compounds of formula (VI) are commercially available or may be prepared according to the methods described in the literature or known to those skilled in the art, adapted as a function of the nature of the substituents R4 and R5. Schemes 9 to 11 below present examples of preparation of the compounds of formula (VI).

For example, when R5 is an alkyl group and R4 contains a heteroaralkyl group, the preparation of compound (VI) may be performed, for example, by following a protocol described in the literature (Durant G. J., Emmet J. C., Ganellin C. R., Roe A. M., (1973) Br. Pat. 1 341 375) as described in scheme 9:

Scheme 9:

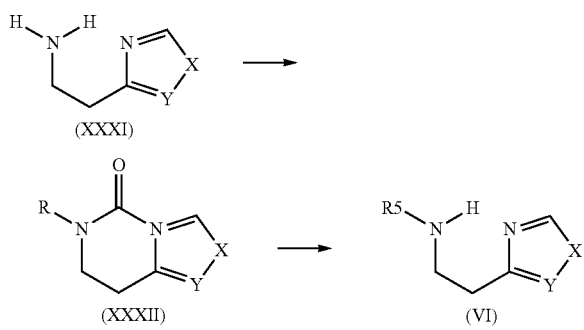

For example, when R4 contains a 1,2,3-triazole heterocycle, the preparation of compound (VI) may be performed according to scheme 10:

Scheme 10:

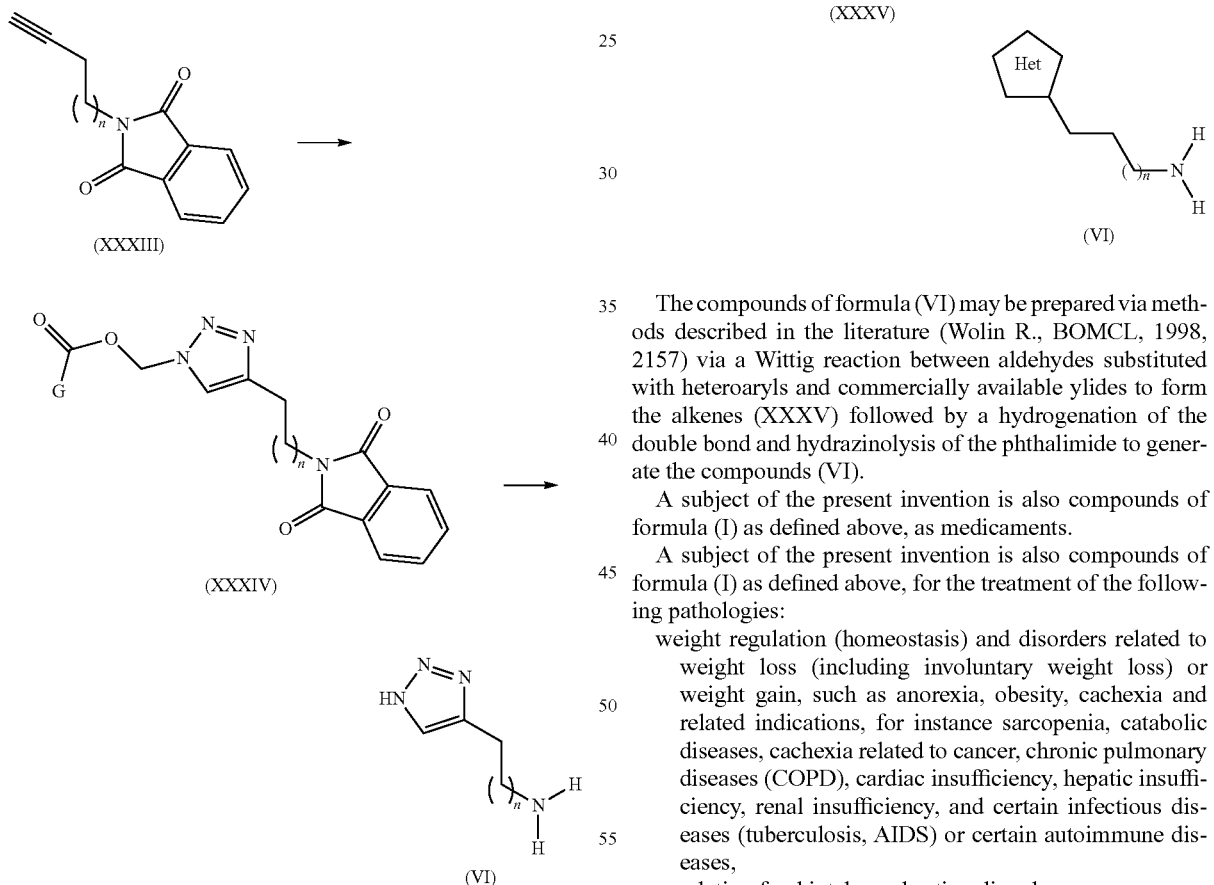

The compounds of formula (XXXIV) may be prepared via methods described in the literature (Loren J. C., Synlett, 2005, 2847-2850) followed by cleavage in basic medium in the presence, for example, of sodium hydroxide, to give the compounds (VI).

For example, when R4 contains a heteroaralkyl, the preparation of compound (VI) may be performed according to scheme 11:

Scheme 11:

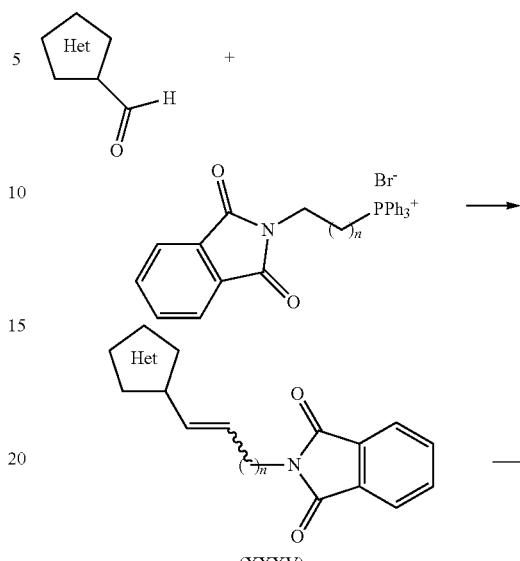

The compounds of formula (VI) may be prepared via methods described in the literature (Wolin R., BOMCL, 1998, 2157) via a Wittig reaction between aldehydes substituted with heteroaryls and commercially available ylides to form the alkenes (XXXV) followed by a hydrogenation of the double bond and hydrazinolysis of the phthalimide to generate the compounds (VI).

A subject of the present invention is also compounds of formula (I) as defined above, as medicaments.

A subject of the present invention is also compounds of formula (I) as defined above, for the treatment of the following pathologies:
  weight regulation (homeostasis) and disorders related to weight loss (including involuntary weight loss) or weight gain, such as anorexia, obesity, cachexia and related indications, for instance sarcopenia, catabolic diseases, cachexia related to cancer, chronic pulmonary diseases (COPD), cardiac insufficiency, hepatic insufficiency, renal insufficiency, and certain infectious diseases (tuberculosis, AIDS) or certain autoimmune diseases,
  regulating food intake and eating disorders,
  bone pathologies.

A subject of the present invention is also the use of the compounds of formula (I) as defined above for the preparation of a composition for treating the following pathologies:
  weight regulation (homeostasis) and disorders related to weight loss (including involuntary weight loss) or weight gain, such as anorexia, obesity, cachexia and related indications, for instance sarcopenia, catabolic diseases, cachexia related to cancer, chronic pulmonary diseases (COPD), cardiac insufficiency, hepatic insufficiency, renal insufficiency, and certain infectious diseases (tuberculosis, AIDS) or certain autoimmune diseases, regulating food intake and eating disorders, bone pathologies.

A subject of the present invention is also a pharmaceutical composition comprising a compound as defined above and a pharmaceutically acceptable support.

A subject of the present invention is also a pharmaceutical composition intended especially for treating the abovementioned complaints, which is characterized in that it comprises, in a pharmaceutically acceptable support that is compatible with the mode of administration selected therefor, a compound of general formula (I) in one of its enantiomers, or a salt thereof with a pharmaceutically acceptable acid.

The term "pharmaceutically acceptable support" means a medium that is compatible with the skin, mucous membranes and the integuments.

The administration of the composition according to the invention may be performed orally, enterally, parenterally, topically or ocularly. Preferably, the pharmaceutical composition is packaged in a form that is suitable for topical application.

Via the oral route, the composition may be in the form of tablets, gel capsules, coated tablets, syrups, suspensions, solutions, powders, granules, emulsions, suspensions, or microspheres, nanospheres or lipid or polymeric vesicles allowing controlled release. Via the parenteral route, the composition may be in the form of solutions or suspensions for perfusion or for injection.

The compounds according to the invention are generally administered orally or systemically at a daily dose from about 0.01 mg/kg to 100 mg/kg of body weight, in one or more dosage intakes.

The compounds are used systemically at a concentration generally of between 0.001% and 10% by weight and preferably between 0.01% and 1% by weight relative to the weight of the composition.

Via the topical route, the pharmaceutical composition according to the invention is more particularly intended for treating the skin and mucous membranes, and may be in liquid, pasty or solid form, and more particularly in the form of ointments, creams, milks, pomades, powders, impregnated pads, syndets, solutions, gels, sprays, mousses, suspensions, sticks, shampoos or washing bases. They may also be in the form of suspensions of microspheres or nanospheres or lipid or polymeric vesicles or of polymeric or gelled patches allowing controlled release.

The compositions used for topical application have a concentration of compound according to the invention generally of between 0.001% and 10% by weight and preferably between 0.01% and 5% by weight relative to the total weight of the composition.

The pharmaceutical and cosmetic compositions as described previously may also contain inert additives or even pharmacodynamically active additives as regards the pharmaceutical compositions, or combinations of these additives, and especially:

wetting agents;
flavour enhancers;
preserving agents such as para-hydroxybenzoic acid esters;
stabilizers;
humidity regulators;
pH regulators;
osmotic pressure modifiers;
emulsifiers;
UV-A and UV-B screening agents;
antioxidants.

Needless to say, a person skilled in the art will take care to select the optional compound(s) to be added to these compositions such that the advantageous properties intrinsically associated with the present invention are not, or are not substantially, adversely affected by the envisaged addition.

Several examples of production of compounds of general formula (I) according to the invention and of the results of biological activity of these compounds will now be given, by way of illustration and without any limiting nature.

The examples that follow describe the preparation of certain compounds in accordance with the invention. These examples are not limiting, and serve merely to illustrate the present invention. The numbers of the presented compounds refer to those given in the table hereinbelow, which illustrates the chemical structures and the physical properties of a number of compounds according to the invention.

The following abbreviations are used:
EDC: 1-Ethyl-(3-Dimethylaminopropyl)Carbodiimide hydrochloride
HOBt: 1-Hydroxy-1,2,3-Benzotriazole
TBTU: N,N,N',N'-TetraMethyl-O-(BenzoTriazol-1-yl) Uronium Tetrafluoroborate
DBU: 1,5-DiazaBicyclo(5,4,0)Undec-5-ene
Rh/Al$_2$O$_3$: Rhodium on alumina
NaHCO$_3$: Sodium hydrogen carbonate
NH$_4$Cl: Ammonium chloride
NH$_4$OH: Ammonium hydroxide
NaCl: Sodium chloride
MgSO$_4$: Magnesium sulfate
Na$_2$SO$_4$: Sodium sulfate
CuSO$_4$: Copper sulfate
NaOH: Sodium hydroxide
EtOAc: Ethyl acetate
DCM: DiChloroMethane
DMF: DiMethylFormamide
MeOH: Methanol
THF: Tetrahydrofuran
DMSO: dimethyl sulfoxide
CH$_3$CN: acetonitrile
TFA: trifluoroacetic acid
CH$_2$Cl$_2$: dichloromethane
CDCl$_3$: deuterated chloroform
TLC: Thin Layer Chromatography Stereoisomers that are converted from one to the other by rotation around the bonds (single bond provided by a pair of electrons) are known as conformers.

EXAMPLE 1

4-Cyclohexyl-1-[2-{3-[2-(1H-imidazol-4-yl)ethyl] ureido}-3-(4-methoxyphenyl)propionyl]piperidine-4-tert-butylcarbamoyl 1-1-1 4-tert-Butylcarbamoyl-4-cyclohexylpiperidine-1-tert-butoxycarbonyl 0.53 ml (1.06 mmol) of a 2M solution of oxalic acid in dichloromethane and 0.04 ml of dimethylformamide are added to 300 mg (0.96 mmol) of piperidine-1-tert-butoxycarbonyl-4-cyclohexyl-4'-carboxylic acid in 3.5 ml of dichloromethane at 0° C. After 1 hour, the solvents are evaporated off. 3.5 ml of tert-butylamine are added and the medium is stirred at room temperature for 6 hours. After evaporating off the solvents, the crude product obtained is chromatographed on silica gel (eluent: 1/1 heptane/ethyl acetate). 285 mg of a white solid are obtained in a yield of 81%.

1-1-2 4-tert-Butylcarbamoyl-4-cyclohexylpiperidine 5 ml of a 4M solution of hydrogen chloride in ethyl acetate are added to 280 mg (1.86 mmol) of 4-tert-butylcarbamoyl-4-cyclohexylpiperidine-1-tert-butoxycarbonyl. After stirring for 4 hours, the reaction medium is washed with aqueous 1N hydrochloric acid solution and then with aqueous sodium hydroxide solution, adjusting the pH to 10. The organic products are extracted with ethyl acetate. After evaporating off the solvents, 172 mg of a white powder are obtained in a yield of 72%.

$^1$H NMR CDCl$_3$: δ=0.80-1.06 (m, 7H); 1.16 (s, 9H); 1.52-1.60 (m, 6H); 1.78-1.85 (m, 2H); 2.62 (bt, 2H, J=12.8 Hz); 2.98 (bd, 2H, J=12.8 Hz)

1-2-1 Methyl (S)-2-amino-3-(4-methoxyphenyl)propionate

To 10 g (33.8 mmol) of (S)-2-tert-butoxycarbonylamino-3-(4-methoxyphenyl)propionic acid are added 75 ml of methanol and then 10 ml of sulfuric acid dropwise over 30 minutes. After 30 hours, the reaction medium is basified to pH 8-9 by adding aqueous 10N sodium hydroxide solution followed by saturated sodium hydrogen carbonate solution. The organic products are extracted with dichloromethane. The organic phase is dried over magnesium sulfate and then filtered, and the solvents are evaporated off. 6.36 g of methyl (S)-2-amino-3-(4-methoxyphenyl)propionate in the form of a brown oil are obtained in a yield of 90%.

1-2-2 Methyl (S)-2-{3-[2-(1H-imidazol-4-yl)ethyl]ureido}-3-(4-methoxyphenyl)-propanoate To 5.08 g (24.3 mmol) of methyl (S)-2-amino-3-(4-methoxyphenyl)propionate are added 15 ml of dichloromethane. The reaction medium is immersed in a bath of cold water. 7.34 g (36.4 mmol) of 4-nitrophenyl chloroformate are added, followed by 6.33 ml of diisopropylethylamine. After warming to room temperature, the reaction medium is stirred for 2 hours. The reaction is stopped by adding water, followed by extraction with dichloromethane. The organic phase is dried over magnesium sulfate, filtered and concentrated on a rotary evaporator. 12 g of a yellow oil are obtained. To these 12 g are added 10 ml of dimethylformamide and the mixture is then heated to 80° C. 8.95 g (48.6 mmol) of histamine dihydrochloride are added, followed by dropwise addition of 14.8 ml (85.1 mmol) of diisopropylethylamine. After cooling to room temperature, the solvents are evaporated off and the crude product is chromatographed on a silica column (eluent: 85/15 dichloromethane/methanol). 5.6 g of methyl (S)-2-{3-[2-(1H-imidazol-4-yl)ethyl]ureido}-3-(4-methoxyphenyl)propanoate in the form of a yellow oil are obtained in a yield of 67%.

$^1$H NMR/CD$_3$OD: δ=2.72 (t, 2H J=6.36 Hz); 2.90 (dd, 1H, J=13.7, 5.88 Hz); 3.04 (dd, 1H, J=13.7, 5.60 Hz); 3.22 (q, 2H, J=7.4 Hz); 3.67 (s, 3H), 3.75 (s, 3H); 4.48 (q, 1H, J=5.76 Hz); 6.81 (d, 2H, J=8.6 Hz); 6.87 (s, 1H); 7.05 (d, 2H, J=8.6 Hz); 7.75 (s, 1H)

1-2-3 2-{3-[2-(1H-Imidazol-4-yl)ethyl]ureido}-3-(4-methoxyphenyl)propanoic acid To 500 mg (1.44 mmol) of methyl (S)-2-{3-[2-(1H-imidazol-4-yl)ethyl]ureido}-3-(4-methoxyphenyl)propanoate are added 500 mg of lithium hydroxide, 7 ml of tetrahydrofuran and 2 ml of water. The reaction medium is placed in a microwave reactor with stirring, at 100° C. for 10 minutes. Seven other identical tests are performed. The various tests are combined and concentrated to dryness. The crude product obtained is purified by filtration on a pad of silica (eluent: 1/1 dichloromethane/methanol). 2.73 g of 2-{3-[2-(1H-imidazol-4-yl)ethyl]ureido}-3-(4-methoxyphenyl)propanoic acid in the form of a pale yellow powder are obtained in a yield of 70%.

$^1$H NMR/CD$_3$OD: δ=2.71 (t, 2H J=6.94 Hz); 2.89 (dd, 1H, J=13.6, 6.67 Hz); 3.05 (dd, 1H, J=13.6, 4.97 Hz); 3.22 (q, 2H, J=7.4 Hz); 3.72 (s, 3H); 4.31 (tl, 1H, J=5.97 Hz); 6.76 (d, 2H, J=8.5 Hz); 6.84 (s, 1H); 7.10 (d, 2H, J=8.5 Hz); 7.68 (s, 1H)

1-3 4-tert-Butylcarbamoyl 4-cyclohexyl-1-[2-{3-[2-(1H-imidazol-4-yl)ethyl]ureido}-3-(4-methoxyphenyl)propionyl]piperidine To 150 mg (0.45 mmol) of 2-{3-[2-(1H-imidazol-4-yl)ethyl]ureido}-3-(4-methoxy-phenyl)propanoic acid dissolved in 3 ml of dichloromethane and 0.5 ml of dimethylformamide are added 0.16 ml (0.90 mmol) of diisopropylethylamine, 161 mg (0.50 mmol) of TBTU and 133 mg (0.50 mmol) of 4-tert-butylcarbamoyl-4-cyclohexylpiperidine. After 3 hours, the solution is washed with 1N sodium hydroxide solution and the organic products are extracted with dichloromethane. The organic phase is dried over magnesium sulfate, filtered and concentrated. The crude product obtained is purified by preparative TLC (eluent: dichloromethane/methanol 85/15). 29 mg of 4-tert-butylcarbamoyl 4-cyclohexyl-1-[2-{3-[2-(1H-imidazol-4-yl)ethyl]ureido}-3-(4-methoxyphenyl)propionyl]-piperidine in the form of a white powder are obtained in a yield of 11%.

$^1$H NMR/DMSO$_{D6}$ 100° C.: δ=0.89-1.17 (m, 7H); 1.29 (s, 9H); 1.34-1.99 (m, 9H); 2.62 (t, J=7.2 Hz, 2H); 2.73-2.89 (m, 4H); 3.24 (ql, J=6-7.6 Hz, 2H); 3.73 (s, 3H); 4.81 (ql, J=6 Hz, 1H); 5.93 (tl, 1H); 6.00 (d, J=8.8 Hz, 1H); 6.23 (s, 1H); 6.74 (s, 1H); 6.81 (d, J=8.4 Hz, 2H); 7.08 (d, J=8 Hz, 2H); 7.47 (s, 1H).

EXAMPLE 2

1-[(R)-2-(4-Butyryl-4-cyclohexylpiperidin-1-yl)-1-(4-methoxybenzyl)-2-oxoethyl]-3-[2-(1-methyl-1H-imidazol-4-yl)ethyl]urea

2-1-1 4-Phenyl-1-(toluene-4-sulfonyl)piperidine-4-carbonitrile 17.2 g (89.8 mmol) of 4-methylbenzenesulfonyl chloride dissolved in 150 ml of dichloromethane are added to a solution of 20 g (89.8 mmol) of 4-phenylpiperidine-4-carbonitrile and 28 ml of triethylamine in 200 ml of dichloromethane. The reaction mixture is stirred for 1 hour at room temperature. The reaction is stopped by adding 200 ml of water, and is then extracted with dichloromethane. The organic phases are combined and dried over sodium sulfate. The solvents are evaporated off and the residue is then taken up in diethyl ether and filtered off. 30.3 g of 4-phenyl-1-(toluene-4-sulfonyl)piperidin-4-carbonitrile in the form of a white powder are obtained in a yield of 99%.

$^1$H NMR/CDCl$_3$: δ=0.60 (t, 3H, J=7.36 Hz); 1.35 (hex, 2H, J=7.36 Hz); 2.09 (t, 2H, J=7.36 Hz); 2.15 (m, 2H); 2.46 (s, 3H); 2.57-2.66 (4H, m); 3.57-3.62 (2H, m); 7.22 (d, 2H, J=8.2 Hz); 7.23-7.46 (m, 5H); 7.71 (d, 2H, J=8.2 Hz)

2-1-2 1-[4-Phenyl-1-(toluene-4-sulfonyl)piperidin-4-yl]-butan-1-one 88 ml (176 mmol) of n-propylmagnesium chloride are added to a solution of 30 g (88 mmol) of 4-phenyl-1-(toluene-4-sulfonyl)piperidine-4-carbonitrile in 500 ml of toluene. The reaction mixture is stirred for 6 hours at 65-70° C. and then overnight at room temperature. The reaction is stopped by adding 100 ml of tetrahydrofuran, and is then hydrolysed with 1N hydrochloric acid solution and extracted with ethyl acetate. The organic phases are combined and dried over sodium sulfate. The solvents are evaporated off and the residue is then taken up in diethyl ether and filtered off. 1.38 g of starting material are recovered. The filtrate is concentrated to dryness and then chromatographed on silica gel (eluent: 80/20 heptane/ethyl acetate). 17.8 g of 1-[4-phenyl-1-(toluene-4-sulfonyl)piperidin-4-yl]-butan-1-one in the form of a white powder are obtained in a yield of 50%.

$^1$H NMR/CDCl$_3$: δ=0.60 (t, 3H, J=7.36 Hz); 1.35 (hex, 2H, J=7.36 Hz); 2.09 (t, 2H, J=7.36 Hz); 2.15 (m, 2H); 2.46 (s, 3H); 2.57-2.66 (4H, m); 3.57-3.62 (2H, m); 7.22 (d, 2H, J=8.2 Hz); 7.23-7.46 (m, 5H); 7.71 (d, J=8.2 Hz)

2-1-3 4-Butyryl-4-phenylpiperidine hydrochloride 10 g (26 mmol) of 1-[4-phenyl-1-(toluene-4-sulfonyl)piperidin-4-yl]-butan-1-one are suspended in 64 ml of sulfuric acid and 32 ml of water. The reaction mixture is stirred at reflux for 48 hours. The reaction is monitored by HPLC. 50 ml of ethanol are added to homogenize the reaction medium, followed by 40 ml of sulfuric acid, and heating is continued for 24 hours. The reaction is stopped by addition to ice and basified with sodium hydroxide solution, and then extracted with ethyl acetate. The organic phases are combined and dried over sodium sulfate. The solvents are evaporated off and the residue is then taken up in diethyl ether and precipitated with a 4N solution of hydrogen chloride in ethyl acetate. 3.8 g of 4-butyryl-4-phenylpiperidine hydrochloride in the form of a white powder are obtained in a yield of 55%.

$^1$H NMR/DMSO: δ=0.56 (t, 3H, J=7.36 Hz); 1.31 (hex, 2H, J=7.36 Hz); 2.21 (m, 2H); 2.27 (t, 2H, J=7.36 Hz); 2.55 (m, 2H); 2.94-2.99 (m, 2H); 3.09-3.12 (m, 2H); 7.32-7.37 (m, 3H); 7.42-7.46 (m, 2H); 8.99 (sl, 1H).

2-1-4 1-(Cyclohexylpiperidin-4-yl)butan-1-one

In a Parr bomb under a hydrogen pressure of 6 bar, 100 mg of rhodium on alumina and 0.2 ml of acetic acid are added to a solution of 100 mg (0.5 mmol) of 4-butyryl-4-phenylpiperidine hydrochloride in 10 ml of dioxane. The reaction medium is heated at 80° C. for 12 hours. The reaction is stopped and then filtered through Celite and washed with dichloromethane. The solvents are evaporated off and the residue is taken up in water, basified with 1N sodium hydroxide solution and extracted with ethyl acetate. The organic phases are dried over sodium sulfate. The solvents are evaporated off and the residue is chromatographed on silica gel (eluent: 9/1 dichloromethane/methanol). 51.2 mg of 1-(4-cyclohexylpiperidin-4-yl)-butan-1-one in the form of a white powder are obtained in a yield of 61%.

$^1$H NMR/CDCl$_3$: δ=0.92 (t, 2H, J=7.36 Hz); 0.98 (m, 2H); 1.07-1.27 (m, 3H); 1.34-1.42 (m, 1H); 1.49-1.68 (m, 5H); 1.62 (hex, 2H, J=7.36 Hz); 1.72-1.82 (m, 2H); 2.02 (ddI, 2H, J=2.28; 13.7 Hz); 2.40 (t, 2H, J=7.36 Hz); 2.55 (td, 2H, J=2.28; 12.4 Hz); 2.95 (dtl, 2H, J=2.96, 12.4 Hz).

2-2 tert-Butyl [(R)-2-(4-butyryl-4-cyclohexylpiperidin-1-yl)-1-(4-methoxybenzyl)-2-oxoethyl]carbamate 0.44 g (1.9 mmol) of 1-(4-cyclohexylpiperidin-4-yl)butan-1-one, 0.56 g of (R)-2-tert-butoxycarbonylamino-3-(4-methoxyphenyl)propionic acid (1.9 mmol), 0.4 g (2.1 mmol) of EDC and 0.282 g (2.1 mmol) of HOBt are dissolved in 4 ml of DMF. The mixture is stirred at room temperature for 2 hours. The solution is washed with aqueous 2.5% citric acid solution and extracted with ethyl acetate, and the organic phase is then washed with aqueous 10N sodium hydroxide solution. It is dried over sodium sulfate, filtered and concentrated. The crude product obtained is chromatographed on silica gel (eluent: 7/3 heptane/ethyl acetate). 0.43 g is obtained in the form of a colourless oil in a yield of 44%.

Figure 2A:
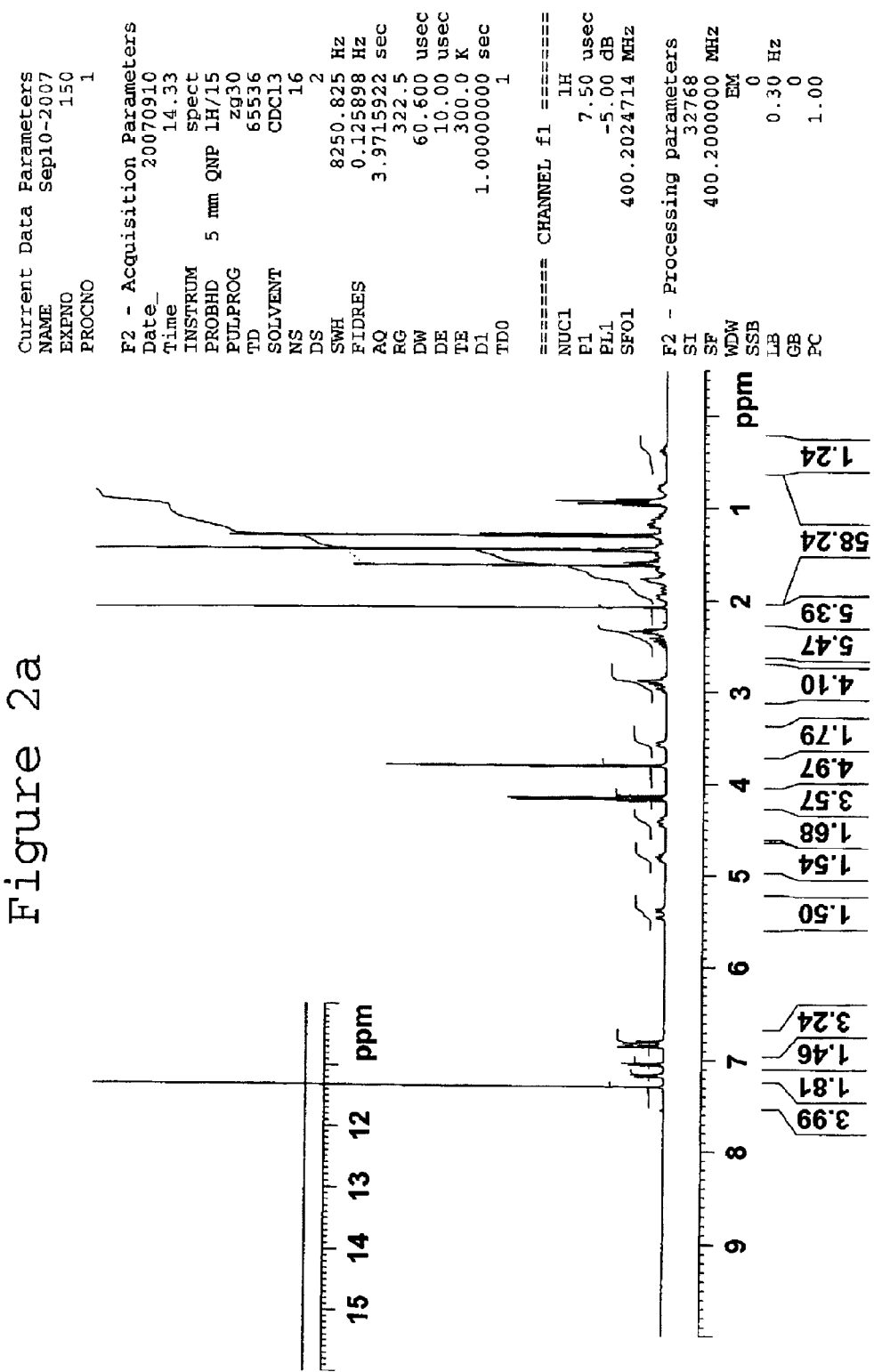
FIG. 2a depicts $^1$H NMR/CDCl$_3$ results for the product of Example 2-2, tert-butyl [(R)-2-(4-butyryl-4-cyclohexylpiperidin-1-yl)-1-(4-methoxybenzyl) -2-oxoethyl]carbamate (mixture of conformers).

$^1$H NMR CDCl$_3$: Results Given in FIG. 2a (Mixture of Conformers)

2-3 1-{1-[(R)-2-Amino-3-(4-methoxyphenyl)propionyl]-4-cyclohexylpiperidin-4-yl}-butan-1-one 0.43 g (0.84 mmol) of tert-butyl [(R)-2-(4-butyryl-4-cyclohexylpiperidin-1-yl)-1-(4-methoxybenzyl)-2-oxoethyl]carbamate is diluted in 8 ml of DCM and 2 ml of trifluoroacetic acid. The solution is stirred for 1 hour 30 minutes at room temperature and then poured into 1N sodium hydroxide solution and extracted with dichloromethane. The organic phase is dried, filtered and then concentrated. 300 mg of 1-{1-[(R)-2-amino-3-(4-methoxyphenyl)propionyl]-4-cyclohexylpiperidin-4-yl}butan-1-one in the form of a colourless oil are obtained in a yield of 86%.

Figure 2B:
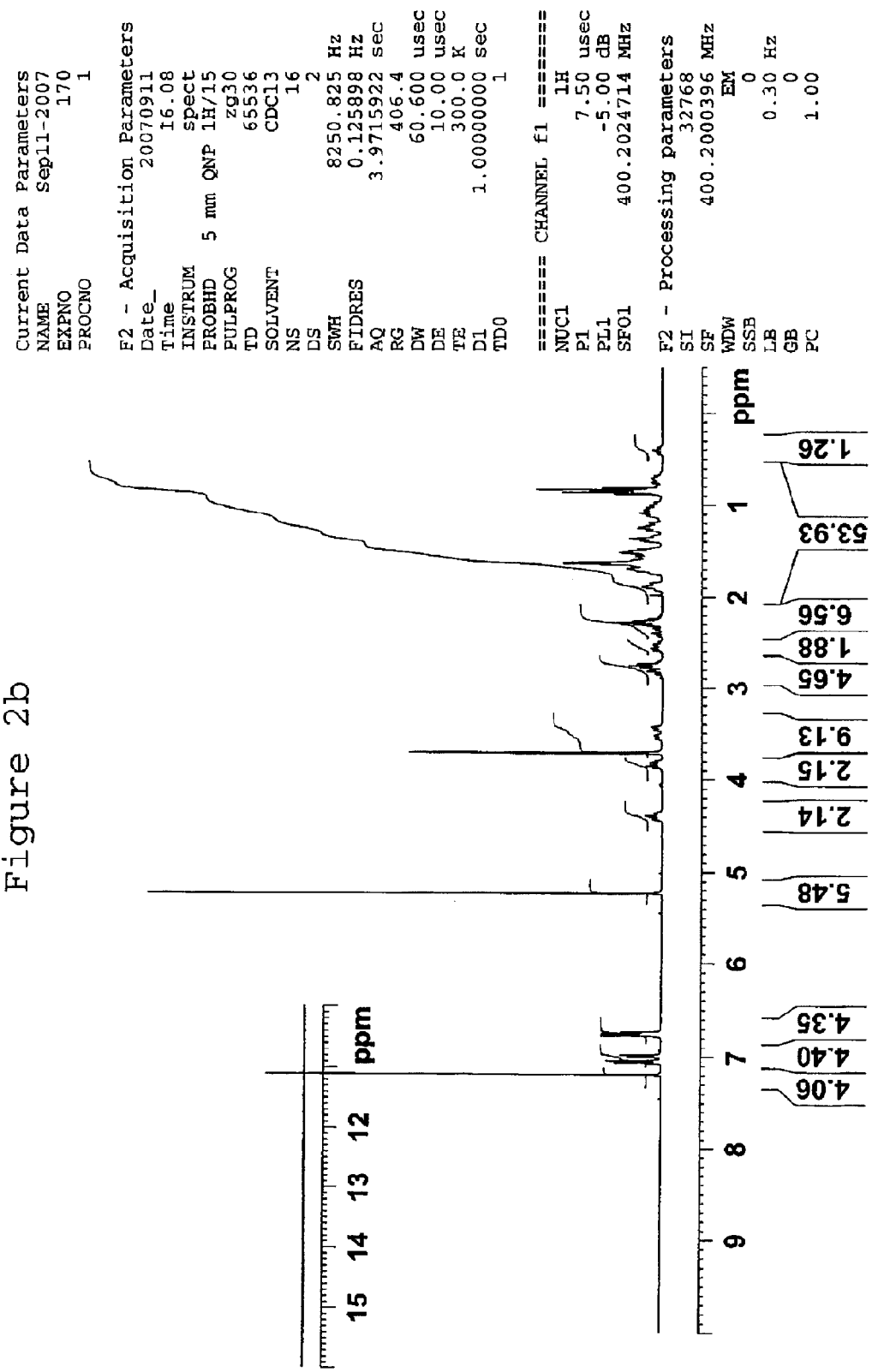
FIG. 2b depicts $^1$H NMR/CDCl$_3$ results for the product of Example 2-3, 1-{1-[(R)-2-amino-3-(4-methoxyphenyl)propionyl]-4-cyclohexylpiperidin -4-yl}butan-1-one (mixture of conformers).

$^1$H NMR CDCl$_3$: Results Given in FIG. 2b Mixture of Conformers)

2-4 1-[(R)-2-(4-Butyryl-4-cyclohexylpiperidin-1-yl)-1-(4-methoxybenzyl)-2-oxoethyl]-3-[2-(1-methyl-1H-imidazol-4-yl)ethyl]urea 75 mg (0.18 mmol) of 1-{1-[(R)-2-amino-3-(4-methoxyphenyl)propionyl]-4-cyclohexylpiperidin-4-yl}butan-1-one and 40 mg (0.2 mmol) of para-nitrophenyl chloroformate are dissolved in 5 ml of dichloromethane. The mixture is stirred for 1 hour at room temperature and the solution is then stopped by adding 20% aqueous ammonia and extracted with dichloromethane. The organic phase is washed with water and then dried over sodium sulfate, filtered and concentrated to dryness. The oil obtained is diluted in 5 ml of DMF, the mixture is heated to 80° C. and 39 mg (0.2 mmol) of 1-methylhistamine and 0.05 ml (0.36 mmol) of triethylamine are then added, and the solution is stirred for 5 minutes at 80° C. and for 10 minutes at room temperature. The reaction is stopped by adding aqueous 1N sodium hydroxide solution and then extracted with DCM. The organic phase is washed with water and then dried over sulfate, filtered and concentrated. The oil obtained is chromatographed on silica gel (eluent: 90/10 DCM/MeOH). 40 mg of 1-[(R)-2-(4-butyryl-4-cyclohexylpiperidin-1-yl)-1-(4-methoxybenzyl)-2-oxoethyl]-3-[2-(1-methyl-1H-imidazol-4-yl)ethyl]urea in the form of a colourless oil are obtained in a yield of 39%.

$^1$H NMR DMSO$_{D6}$ 100° C.: 0.80-0.90 (m, 5H); 1.04-1.22 (m, 4H); 1.32-1.54 (m, 6H); 1.59-1.62 (m, 1H); 1.72 (bd, 2H, J=13.2 Hz); 1.89 (bt, 2H, J=13.2 Hz); 2.40 (t, 2H, J=7.2 Hz); 2.54 (t, 2H, J=7.2 Hz); 2.71 (dd, 1H, J=8.0, 13.6 Hz); 2.79 (dd, 1H, J=13.6, 5.6 Hz); 3.2 (m, 4H); 3.22 (q, 2H, J=7.2 Hz); 3.59 (s, 3H); 3.73 (s, 3H); 4.79 (q, 1H, J=4.3 Hz); 5.89 (vs, 1H);

5.98 (bd, J=7.2 Hz); 6.76 (s, 1H); 6.81 (d, 2H, J=8.0 Hz); 7.07 (d, 2H, J=8.0 Hz); 7.39 (s, 1H).

EXAMPLE 3

1-[(R)-2-(4-Butyryl-4-cyclohexylpiperidin-1-yl)-1-(4-methoxybenzyl)-2-oxoethyl]-3-[2-(1H-[1,2,3]triazol-4-yl)ethyl]urea 3-1-1 2,2-Dimethylpropionic acid 4-[2-(1,3-dioxo-1,3-dihydroisoindol-2-yl)ethyl]-[1,2,3]triazol-1-ylmethyl ester 702 mg (3.52 mmol) of N-(3-butynyl)phthalimide and 552 mg (3.51 mmol) of 2,2-dimethylpropionic acid azidomethyl ester are suspended in a water/t-butanol mixture (1/1, 10.5 ml). 0.18 ml of a 1M $CuSO_4$ solution is added. 206 mg (1.04 mmol) of sodium ascorbate are then added. After 4 hours, the reaction is stopped by adding aqueous ammonia solution, and the reaction medium is extracted with EtOAc. The organic phase is then washed with brine and dried over $MgSO_4$, filtered and concentrated. 1.11 g of 2,2-dimethylpropionic acid 4-[2-(1,3-dioxo-1,3-dihydroisoindol-2-yl)ethyl]-[1,2,3]triazol-1-ylmethyl ester in the form of a yellow oil are obtained in a yield of 88%.

3-1-2 2-(1H-[1,2,3]Triazol-4-yl)ethylamine dihydrochloride 1.08 g (3.03 mmol) of 2,2-dimethylpropionic acid 4-[2-(1,3-dioxo-1,3-dihydroisoindol-2-yl)ethyl]-[1,2,3]triazol-1-ylmethyl ester are dissolved in 7 ml of MeOH, to which 7 ml of aqueous 1N sodium hydroxide solution are added. After stirring for 2 hours, the reaction medium is extracted with DCM. The aqueous phase is concentrated. The solid obtained is taken up in ethanol and, after filtration, the solvents are evaporated off. The crude product is purified in a column of silica (7/3 DCM/MeOH). 558 mg of a white solid are obtained and dissolved in 15 ml of THF and 6 ml of water, to which are added 720 mg of lithium hydroxide. The reaction medium is placed at 160° C. in a microwave reactor for 45 minutes. The reaction medium is filtered and then extracted with DCM. The aqueous phase is then acidified with hydrochloric acid (pH=1) and is then concentrated. The crude product obtained is chromatographed on silica gel (eluent: 7/3 DCM/MeOH). 430 mg of 2-(1H-[1,2,3]triazol-4-yl)ethylamine dihydrochloride are obtained in the form of a white powder in a yield of 14%.

$^1$H NMR DMSO: 2.93 (m, 2H); 3.02 (m, 2H); 7.76 (s, 1H)

3-2 1-[(R)-2-(4-Butyryl-4-cyclohexylpiperidin-1-yl)-1-(4-methoxybenzyl)-2-oxoethyl]-3-[2-(1H-[1,2,3]triazol-4-yl)ethy]urea 30 mg (0.15 mmol) of 4-nitrophenyl chloroformate are added, at 0° C., to 57 mg (0.14 mmol) of 1-{1-[(R)-2-amino-3-(4-methoxyphenyl)propionyl]-4-cyclohexylpiperidin-4-yl}butan-1-one (cf. preparation 2-3) dissolved in 2 ml of DCM. The reaction mixture is stirred for 4 hours at room temperature. The reaction is stopped by adding aqueous $NH_4OH$ solution and the organic compounds are extracted with DCM. The organic phase is then washed with water and dried over $MgSO_4$, filtered and concentrated. The oil obtained is dissolved in DMF at 80° C., and 52 mg (0.28 mmol) of 2-(1H-[1,2,3]triazol-4-yl)ethylamine dihydrochloride and 0.1 ml (0.72 mmol) of triethylamine are then added. The reaction mixture is stirred at 80° C. for 10 minutes. After cooling to room temperature, dichloromethane is added and the organic phase is washed with 1N sodium hydroxide. The organic phase is dried over $MgSO_4$, filtered and concentrated. The crude product obtained is chromatographed on silica gel (eluent: 93/7 DCM/MeOH). 25 mg of 1-[(R)-2-(4-butyryl-4-cyclohexylpiperidin-1-yl)-1-(4-methoxybenzyl)-2-oxoethyl]-3-[2-(1H-[1,2,3]triazol-4-yl)ethyl]urea are obtained in the form of a white solid in a yield of 32%.

HPLC:
Atlantis T3 150×4.6 mm, 5 µm column
UV detector: 190-450 nm
Flow rate: 0.3 ml/min
Solvent A: H2O+0.05 TFA
Solvent B: CH3CN+0.05 TFA
Gradient:

| Time | composition |
|---|---|
| 0.0 min | A = 95%, B = 5% |
| 20.0 min | A = 5%, B = 95% |
| 30.0 min | A = 5%, B = 95% |

Retention time: 17.44 min, 97%, M+H: 553.

EXAMPLE 4

Ethyl 4-cyclohexyl-1-[(R)-2-{3-[3-(3H-imidazol-4-yl)propyl]-ureido}-3-(4-methoxyphenyl)propionyl]piperidine-4-carboxylate 4-1-1 Ethyl piperidine-1-tert-butoxycarbonyl-4-cyclohexyl-4'-carboxylate 1.92 ml (12.8 mmol) of DBU and 1.04 ml (12.8 mmol) of iodoethane are added to 2.00 g (6.42 mmol) of piperidine-1-tert-butoxycarbonyl-4-cyclohexyl-4'-carboxylic acid in 10 ml of toluene. The medium is stirred in a microwave reactor for 10 minutes at 120° C. Dichloromethane is added to the reaction medium and the organic phase is washed with a saturated aqueous $NaHCO_3$ solution. The organic phase is dried over $MgSO_4$, filtered and concentrated. The crude product obtained is chromatographed on silica gel (eluent: 9/1 heptane/ethyl acetate). 1.92 g of ethyl piperidine-1-tert-butoxycarbonyl-4-cyclohexyl-4'-carboxylate in the form of a colourless oil are obtained in a yield of 88%.

4-1-2 Ethyl piperidine-4-cyclohexyl-4'-carboxylate 6 ml of trifluoroacetic acid are introduced at 0° C. into 1.90 g (5.60 mmol) dissolved in 8 ml of dichloromethane. After 4 hours, the solvents are evaporated off and the reaction medium is taken off in EtOAc and then washed with 1N sodium hydroxide. The organic phase is dried over $MgSO_4$, filtered and evaporated. 1.21 g of ethyl piperidine-4-cyclohexyl-4'-carboxylate in the form of a white solid are obtained in a yield of 90%.

$^1$H NMR $CDCl_3$: 1.07-1.17 (m, 6H); 1.21 (t, 3H, J=7.2 Hz); 1.25-1.33 (m, 1H); 1.45 (dt, 2H, J=13.4, 4.16 Hz); 1.56-1.71 (m, 5H); 2.09 (bd, 2H, J=13.6 Hz); 2.61 (bt, 2H, J=12.8 Hz), 3.03 (bd, 2H, J=12.8 Hz); 4.12 (q, 2H, J=7.12 Hz)

4-2 3-(1H-Imidazol-4-yl)propylamine bis(trifluoroacetate)

2 ml of trifluoroacetic acid are added to 195 mg (0.53 mmol) of 3-(1-trityl-1H-imidazol-4-yl) propylamine dissolved in 8 ml of DCM and then immersed in an ice bath. After warming to room temperature, the reaction medium is stirred for 2 hours and the solvents are then evaporated off. The solid obtained is taken up in EtOAc and water. The aqueous phase is then concentrated and 110 mg of a white powder are obtained and used in the next step without further purification.

$^1$H NMR DMSO: 2.09 (pent, 2H, J=6.9 Hz); 2.77-2.82 (m, 2H); 4.28 (t, 2H, J=6.8 Hz); 7.71 (s, 1H); 7.77 (s, 1H); 9.11 (s, 1H)

4-3 Ethyl 1-[(R)-2-tert-butoxycarbonylamino-3-(4-methoxyphenyl)propionyl]-4-cyclohexylpiperidine-4-carboxylate To 3.22 g (10.9 mmol) of (R)-2-tert-butoxycarbonylamino-3-(4-methoxyphenyl)-propionic acid dissolved in 20 ml of DMF are added 2.29 g (12.0 mmol) of EDC, 1.62 g (12.0 mmol) of HOBt, 2.62 g (10.9 mmol) of ethyl 4-cyclohexylpiperidine-4-carboxylate and 4.6 ml (32.7 mmol) of triethylamine. After stirring for 2 hours 30 minutes, the reaction is stopped by adding aqueous 1N sodium hydroxide solution and the organic products are extracted with dichloromethane. The organic phase is dried over MgSO$_4$, filtered and evaporated. The crude product obtained is chromatographed on silica gel (eluent: 7/3 heptane/EtOAc). 3.70 g of ethyl 1-[(R)-2-tert-butoxycarbonylamino-3-(4-methoxyphenyl)propionyl]-4-cyclohexylpiperidine-4-carboxylate in the form of a white powder are obtained in a yield of 66%.

$^1$H NMR/CDCl$_3$: results presented in FIG. 3a (mixture of conformers)

4-4 Ethyl 1-[(R)-2-amino-3-(4-methoxyphenyl)propionyl]-4-cyclohexylpiperidine-4-carboxylate To 3.7 g (7.16 mmol) of ethyl 1-[(R)-2-tert-butoxycarbonylamino-3-(4-methoxy-phenyl)propionyl]-4-cyclohexylpiperidine-4-carboxylate dissolved in 30 ml of DCM immersed in a bath at 0° C. are added 10 ml of trifluoroacetic acid. After stirring for 1 hour 30 minutes, the solvents are evaporated off. The reaction medium is washed with aqueous 1N sodium hydroxide solution and extracted with DCM. The organic phase is then washed with water and then dried over MgSO$_4$, filtered and concentrated. 2.74 g of ethyl 1-[(R)-2-amino-3-(4-methoxyphenyl)propionyl]-4-cyclohexylpiperidine-4-carboxylate in the form of a white powder are obtained in a yield of 92%.

Figure 3B:
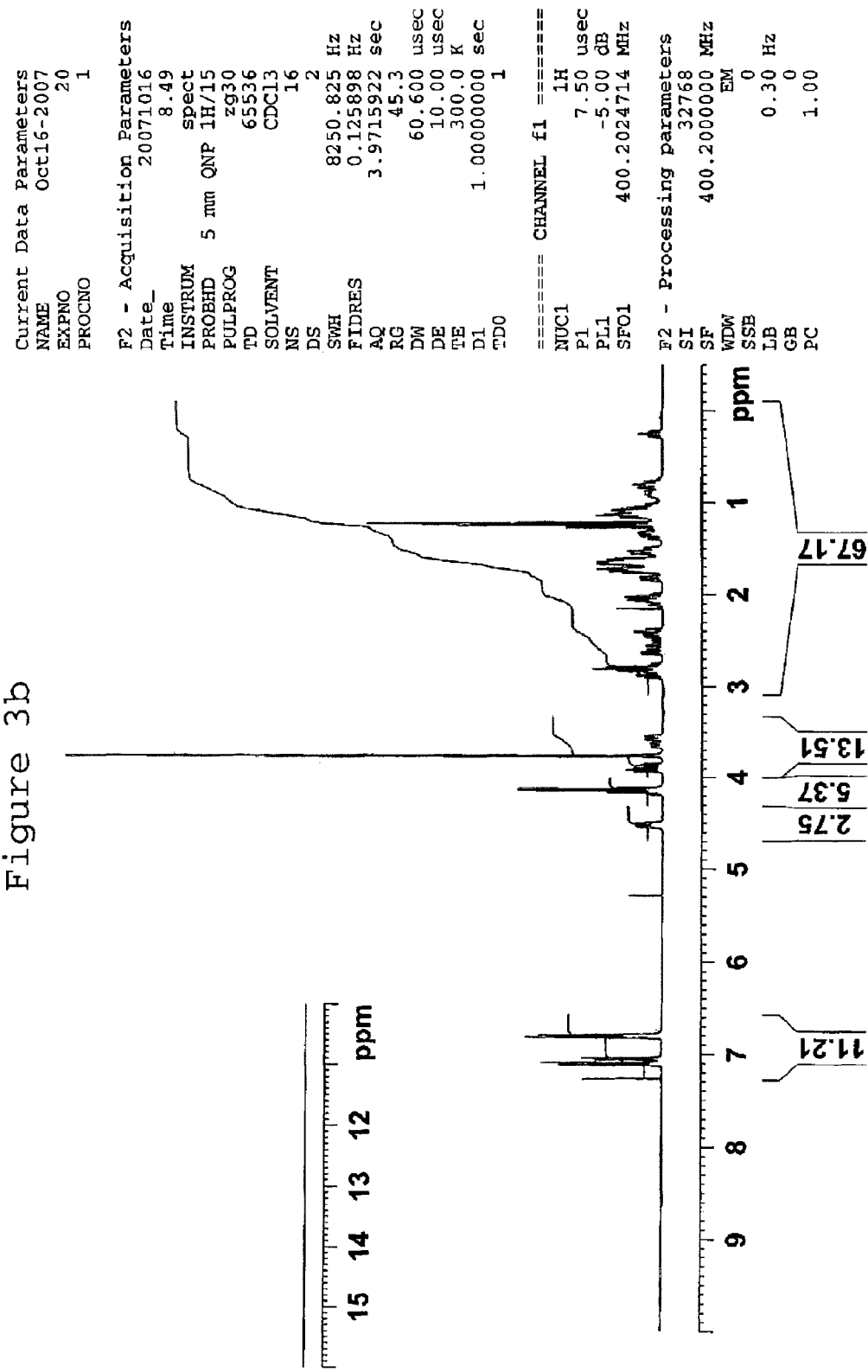
FIG. 3b depicts $^1$H NMR/CDCl$_3$ results for the product of Example 4-4, ehtyl-1-[(R)-2-amino-3-(4-methoxyphenyl)propionyl]-4-cyclohexylpiperidine-4-carboxylate (mixture of conformers).

$^1$H NMR/CDCl$_3$: results presented in FIG. 3b (mixture of conformers)

4-5 Ethyl 4-cyclohexyl-1-[(R)-2-{3-[3-(3H-imidazol-4-yl)propyl]ureido}-3-(4-methoxy-phenyl)propionyl]piperidine-4-carboxylate To 100 mg (0.24 mmol) of ethyl 1-[(R)-2-amino-3-(4-methoxyphenyl)propionyl]-4-cyclohexylpiperidine-4-carboxylate dissolved in 2 ml of DCM immersed in a bath of cold water are added 53 mg (0.26 mmol) of 4-nitrophenyl chloroformate. After warming to room temperature, the reaction medium is stirred for 2 hours and 30 minutes. The reaction is stopped by adding aqueous ammonia solution. The organic phase is then washed with water and then dried over MgSO$_4$, filtered and concentrated. The oil obtained is dissolved in 4 ml of DMF at 80° C., and 110 mg (0.31 mmol) of 3-(1H-imidazol-4-yl)propylamine bis(trifluoroacetate), 0.05 ml of triethylamine are then added. The reaction mixture is left stirring at 80° C. for 15 minutes. After returning to room temperature, dichloromethane is added and the organic phase is washed with 1N sodium hydroxide solution. The organic phase is dried over MgSO$_4$, filtered and concentrated. The crude product obtained is chromatographed on silica gel (eluent: 9/1 DCM/MeOH). 26 mg of ethyl 4-cyclohexyl-1-[(R)-2-{3-[3-(3H-imidazol-4-yl)propyl]ureido}-3-(4-methoxyphenyl)propionyl]-piperidine-4-carboxylate in the form of a colourless oil are obtained in a yield of 11%.

Figure 3C:
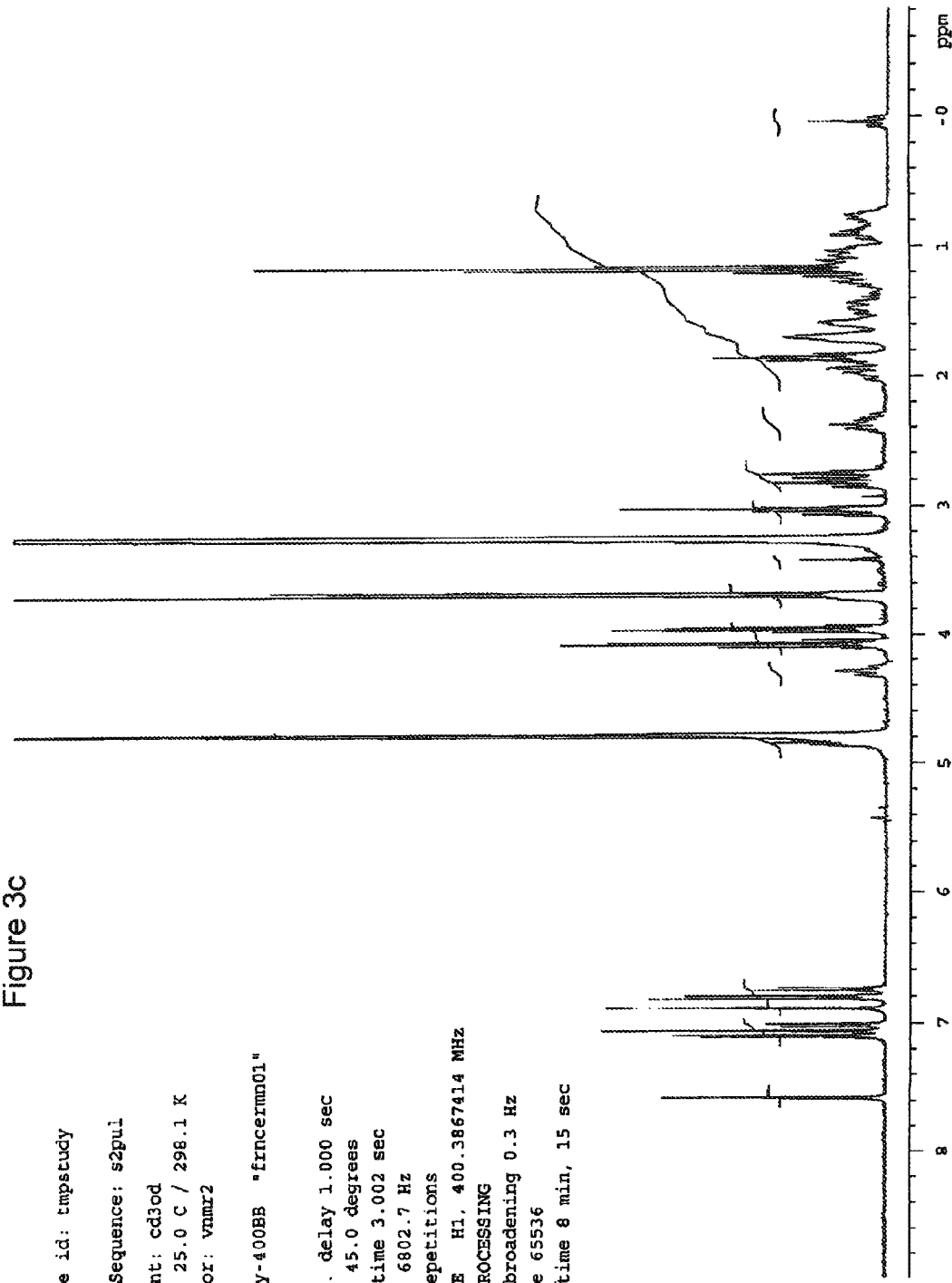
FIG. 3c depicts $^1$H NMR results for the product of Example 4-5, ethyl 4-cyclohexyl-1 -[(R)-2-{3[3-(3H-imidazol-4-yl)propyl]ureido}-3-(4-methoxyphenyl)propionyl]piperidine-4-carboxylate (mixture of conformers).

$^1$H NMR: results presented in FIG. 3c (mixture of conformers)

EXAMPLE 5

Ethyl 4-cyclohexyl-1-((R)-3-(3,4-dichlorophenyl)-2-{3-[2-(1H-imidazol-4-yl)ethyl]ureido}propionyl) piperidine-4-carboxylate

5-1 Ethyl 1-[(R)-2-tert-butoxycarbonylamino-3-(3,4-dichlorophenyl)propionyl]-4-cyclohexylpiperidine-4-carboxylate 0.5 g (2.1 mmol) of ethyl piperidine-4-cyclohexyl-4'-carboxylate (cf. preparation 4-1-2), 0.7 g (2.1 mmol) of (R)-2-tert-butoxycarbonylamino-3-(3,4-dichlorophenyl)-propionic, 0.31 g (2.3 mmol) of HOBT, 0.44 g (2.3 mmol) of EDC and 0.73 ml (4.2 mmol) of diisopropylethylamine are placed in 5 ml of DMF. The mixture is stirred for 2 hours at room temperature. The reaction is stopped by addition of an aqueous 5% citric acid solution. The organic compounds are extracted with ethyl acetate, then the organic phase is washed with aqueous 1N sodium hydroxide solution and then with water. The organic phase is dried over sodium sulfate, filtered and concentrated. The oil obtained is chromatographed on silica gel (eluent: 1/1 heptane/ethyl acetate). 300 mg of ethyl 1-[(R)-2-tert-butoxycarbonylamino-3-(3,4-dichlorophenyl) propionyl]-4-cyclohexylpiperidine-4-carboxylate are obtained in a yield of 26%.

Figure 4:
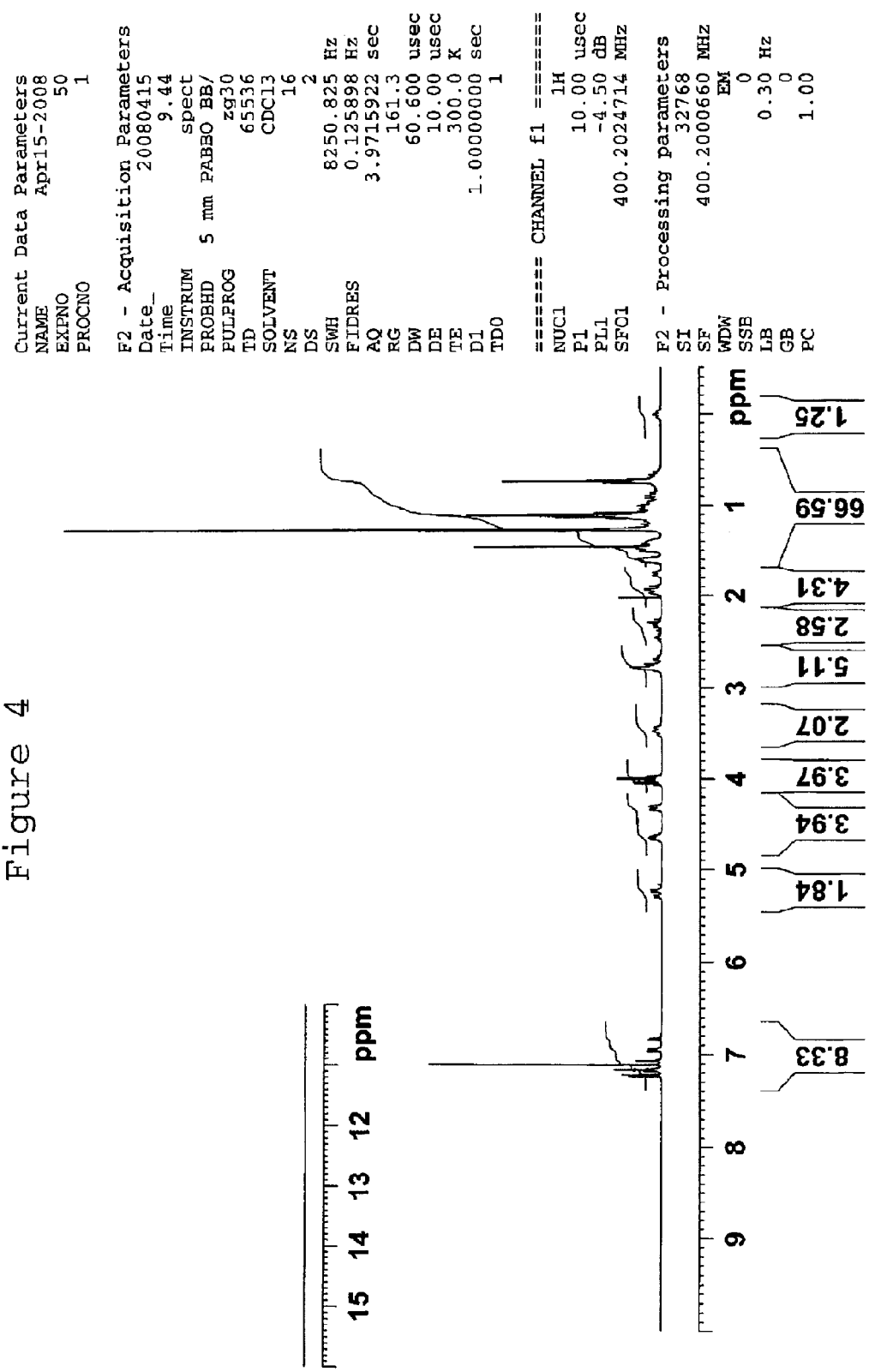
FIG. 4 depicts $^1$H NMR/CDCl$_3$ results for the product of Example 5-1, ethyl 1-[(R)-2-tert-butoxycarbonylamino-3-(3, 4-dichlorophenyl)propionyl]-4-cyclohexylpiperidine -4-carboxylate (mixture of conformers).

$^1$H NMR CDCl$_3$: results given in FIG. 4 (mixture of conformers)

5-2 Ethyl 1-[(R)-2-amino-3-(3,4-dichlorophenyl) propionyl]-4-cyclohexylpiperidine-4-carboxylate 300 mg (0.54 mmol) of ethyl 1-[(R)-2-tert-butoxycarbonylamino-3-(3,4-dichloro-phenyl)propionyl]-4-cyclohexylpiperidine-4-carboxylate are diluted in 5 ml of a 4/1 dichloromethane/trifluoroacetic acid solution. After stirring for 2 hours, the mixture is poured into aqueous 1N sodium hydroxide solution and then extracted with dichloromethane. The organic phase is dried over sodium sulfate, filtered and concentrated. 210 mg of ethyl 1-[(R)-2-amino-3-(3,4-dichlorophenyl)propionyl]-4-cyclohexylpiperidine-4-carboxylate in the form of a white powder are obtained in a yield of 86%.

5-3 Ethyl 4-cyclohexyl-1-((R)-3-(3,4-dichlorophenyl)-2-{3-[2-(1H-imidazol-4-yl)ethyl]-ureido}propionyl)piperidine-4-carboxylate 60 mg (11 mmol) of ethyl 1-[(R)-2-amino-3-(3,4-dichlorophenyl)propionyl]-4-cyclohexylpiperidine-4-carboxylate and 29 mg (0.12 mmol) of para-nitrophenyl chloroformate are dissolved in 5 ml of dichloromethane. The mixture is stirred for 1 hour at room temperature and the solution is then poured into water and extracted with dichloromethane. The organic phase is dried over sodium sulfate, filtered and concentrated. The colourless oil obtained is diluted in 5 ml of dimethylformamide, the mixture is heated to 80° C., and 18 mg (0.12 mmol) of histamine are added and the solution is stirred for 5 minutes at 80° C. and overnight at room temperature. The reaction is stopped by adding aqueous 1N sodium hydroxide solution and the organic compounds are extracted with dichloromethane. The organic phase is washed with water and then dried over sodium sulfate, filtered and concentrated. The oil obtained is chromatographed on silica gel (eluent: 90/10 DCM/MeOH). 25 mg of ethyl 4-cyclohexyl-1-((R)-3-(3,4-dichlorophenyl)-2-{3-[2-(1H-imidazol-4-yl)ethyl]ureido}-propionyl)piperidine-4-carboxylate in the form of a colourless oil are obtained in a yield of 38%.

$^1$H NMR/DMSO 100° C.: 0.89 (m, 4H); 1.11 (m, 4H); 1.22 (t, 3H, 6 Hz); 1.28 (s, 2H); 1.61 (d, 3H, 8 Hz); 1.73 (d, 2H, 12 Hz); 1.97 (t, 2H, 8 Hz); 2.62 (t, 2H, 6 Hz); 2.87 (m, 6H); 3.24 (qua, 2H, 6 Hz); 4.13 (qua, 2H, 8 Hz); 4.85 (qua, 2H 8 Hz); 5.94 (m, 1H); 6.09 (d, 1H, 8 Hz); 6.76 (d, 1H, 8 Hz); 7.18 (d, 1H, 8 Hz); 7.40 (s, 1H); 7.47 (d, 1H, 8 Hz); 7.53 (s, 1H)

EXAMPLE 6

Ethyl 4-cyclohexyl-1-((R)-3-(3,4-dichlorophenyl)-2-{3-[2-(3-methyl-3H-imidazol-4-yl)ethyl]ureido}propionyl)piperidine-4-carboxylate Synthetic route identical to that of Example 5.
$^1$H NMR/DMSO 100° C.: 0.89 (m, 3H); 1.05-1.45 (m, 8H); 1.22 (t, 3H, 6 Hz); 1.61 (m, 3H); 1.75 (m, 2H); 1.97 (m, 2H); 2.64 (m, 2H); 2.78 (m, 2H); 2.80-3.10 (m, 4H); 3.24 (m, 2H); 3.56 (s, 3H); 4.15 (qua, 2H, 8 Hz); 4.87 (qua, 2H 8 Hz); 6.02 (m, 1H); 6.14 (d, 1H, 8 Hz); 6.78 (d, 1H, 8 Hz); 7.18 (d, 1H, 8 Hz); 7.40 (s, 1H); 7.48 (d, 1H, 8 Hz); 7.66 (s, 1H)

EXAMPLE 7

Ethyl 4-cyclohexyl-1-[(R)-2-{3-[3-(1H-imidazol-4-yl)propyl]-thioureido}-3-(4-methoxyphenyl)propionyl]piperidine-4-carboxylate 7-1 Ethyl 1-[(R)-2-amino-3-(4-methoxyphenyl)propionyl]-4-cyclohexylpiperidine-4-carboxylate trifluoroacetate To 10 g (19.4 mmol) of ethyl 1-[(R)-2-tert-butoxycarbonylamino-3-(4-methoxyphenyl)-propionyl]-4-cyclohexylpiperidine-4-carboxylate (cf. preparation 4-3) in 80 ml of dichloromethane are added 20 ml of trifluoroacetic acid. The reaction medium is stirred for 2 hours at room temperature. The solvents are evaporated off and diethyl ether is added in the presence of a few drops of dichloromethane. The precipitate obtained is filtered off and then dried under vacuum at 40° C. 8 g of ethyl 1-[(R)-2-amino-3-(4-methoxyphenyl)propionyl]-4-cyclohexylpiperidine-4-carboxylate trifluoroacetate in the form of a white powder are obtained in a yield of 78%.

Figure 5A:
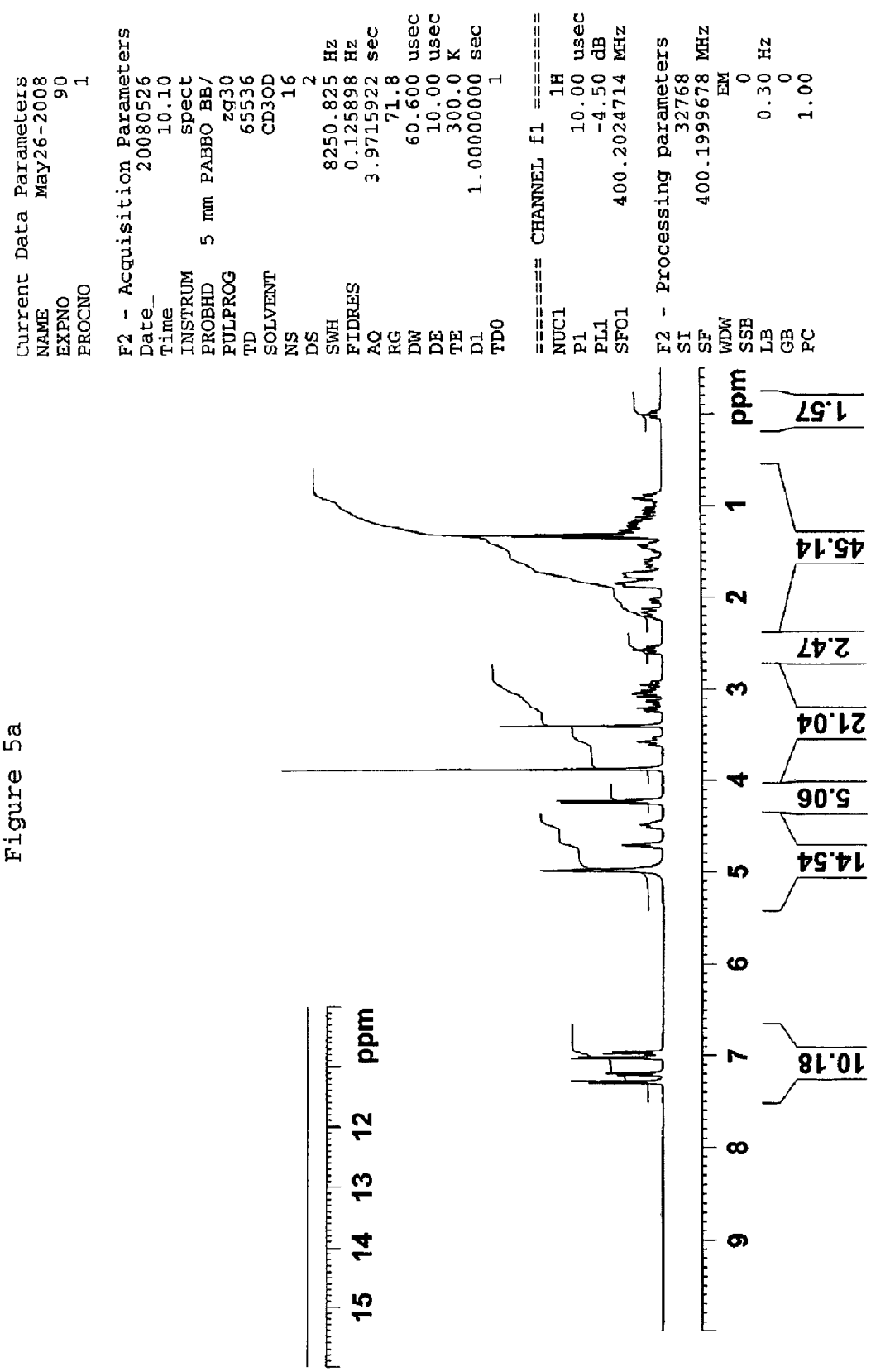
FIG. 5a depicts $^1$H NMR/CD$_3$OD results for the product of Example 7-1, ehtyl 1-[(R)-2-amino-3-(4-methoxyphenyl)propionyl]-4-cyclohexylpiperidine-4-caroxylate trifluoroacetate (mixture of conformers).

$^1$H NMR/CD$_3$OD: results presented in FIG. 5a (mixture of conformers)

7-2 Ethyl 4-cyclohexyl-1-[(R)-2-isothiocyanato-3-(4-methoxyphenyl)propionyl]-piperidine-4-carboxylate To 1 g (1.88 mmol) of ethyl 1-[(R)-2-amino-3-(4-methoxyphenyl)propionyl]-4-cyclohexylpiperidine-4-carboxylate trifluoroacetate dissolved in 10 ml of CH$_2$Cl$_2$ and 1 ml (5.66 mmol) of diisopropylethylamine are added 438 mg (1.88 mmol) of thiocarbonic acid O,O-bis(2-pyridyl) ester. After stirring the reaction medium for 2 hours at room temperature, the solvents are evaporated off and the crude product obtained is chromatographed on silica gel (eluent: 6/4 heptane/EtOAc). 763 mg of ethyl 4-cyclohexyl-1-[(R)-2-isothiocyanato-3-(4-methoxyphenyl)propionyl]piperidine-4-carboxylate in the form of a colourless oil are obtained in a yield of 88%.

Figure 5B:
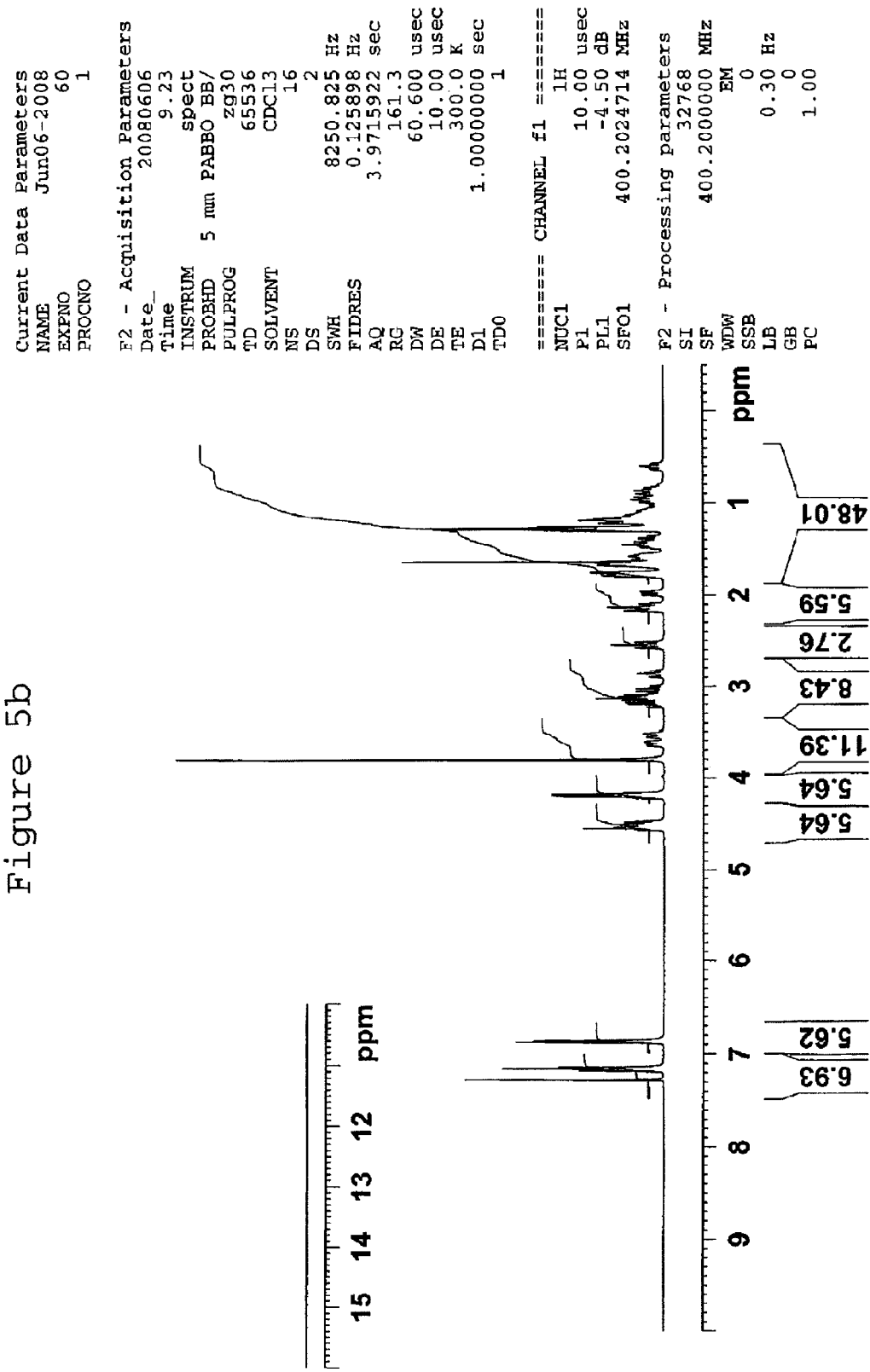
FIG. 5b depicts $^1$H NMR/CDCl$_3$ results for the product of Example 7-2, ethyl 4-cyclohexyl-1-[(R)-2-isothiocyanato-3-(4-methoxyphenyl)propionyl]piperidine-4-carboxylate (mixture of conformers).

$^1$H NMR/CDCl$_3$: results presented in FIG. 5b (mixture of conformers)

7-3 Ethyl 4-cyclohexyl-1-[(R)-2-{3-[3-(1H-imidazol-4-yl)propyl]thioureido}-3-(4-methoxyphenyl) propionyl]piperidine-4-carboxylate To 65 mg (0.141 mmol) of ethyl 4-cyclohexyl-1-[(R)-2-isothiocyanato-3-(4-methoxy-phenyl)propionyl]piperidine-4-carboxylate in 5 ml of DMF are added 50 mg (0.141 mmol) of 3-(1H-imidazol-4-yl)propylamine bis(trifluoroacetate) (cf. preparation 4-2) and then 0.063 ml (0.425 mmol) of 1,8-diazabicyclo[5.4.0]undec-7-ene. The reaction medium is stirred for 2 hours and then hydrolysed by adding aqueous 5% citric acid solution. The organic compounds are extracted with dichloromethane. The organic phase is dried over MgSO$_4$, filtered and concentrated. The crude product obtained is chromatographed on silica gel (eluent: 80/20 CH$_2$Cl$_2$/MeOH). 22 mg of ethyl 4-cyclohexyl-1-[(R)-2-{3-[2-(1H-imidazol-4-yl)propyl]thioureido}-3-(4-methoxyphenyl)propionyl]piperidine-4-carboxylate in the form of a pale yellow powder are obtained in a yield of 26%.

Figure 5C:
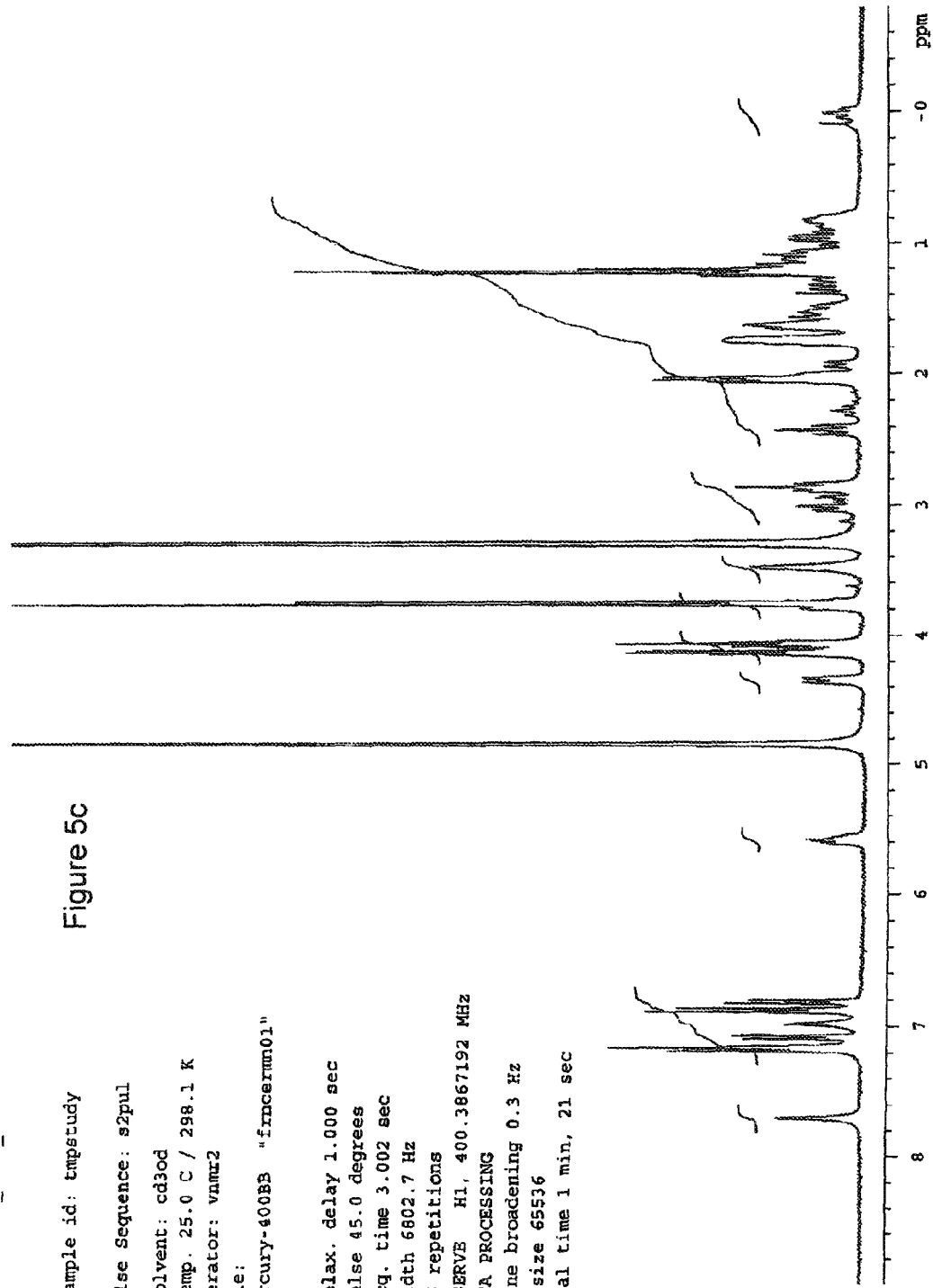
FIG. 5c depicts $^1$H NMR results for the product of Example 7-3, ethyl 4-cyclohexyl-1-[(R)-2-{3]43-(1H-imadazol-4-yl)propyl]thioureido}-3-(4-methoxyphenyl) propionyl]piperidine-4-carboxylate (mixture of conformers).

$^1$H NMR: results presented in FIG. 5c (mixture of conformers).

EXAMPLE 8

Figure 6:
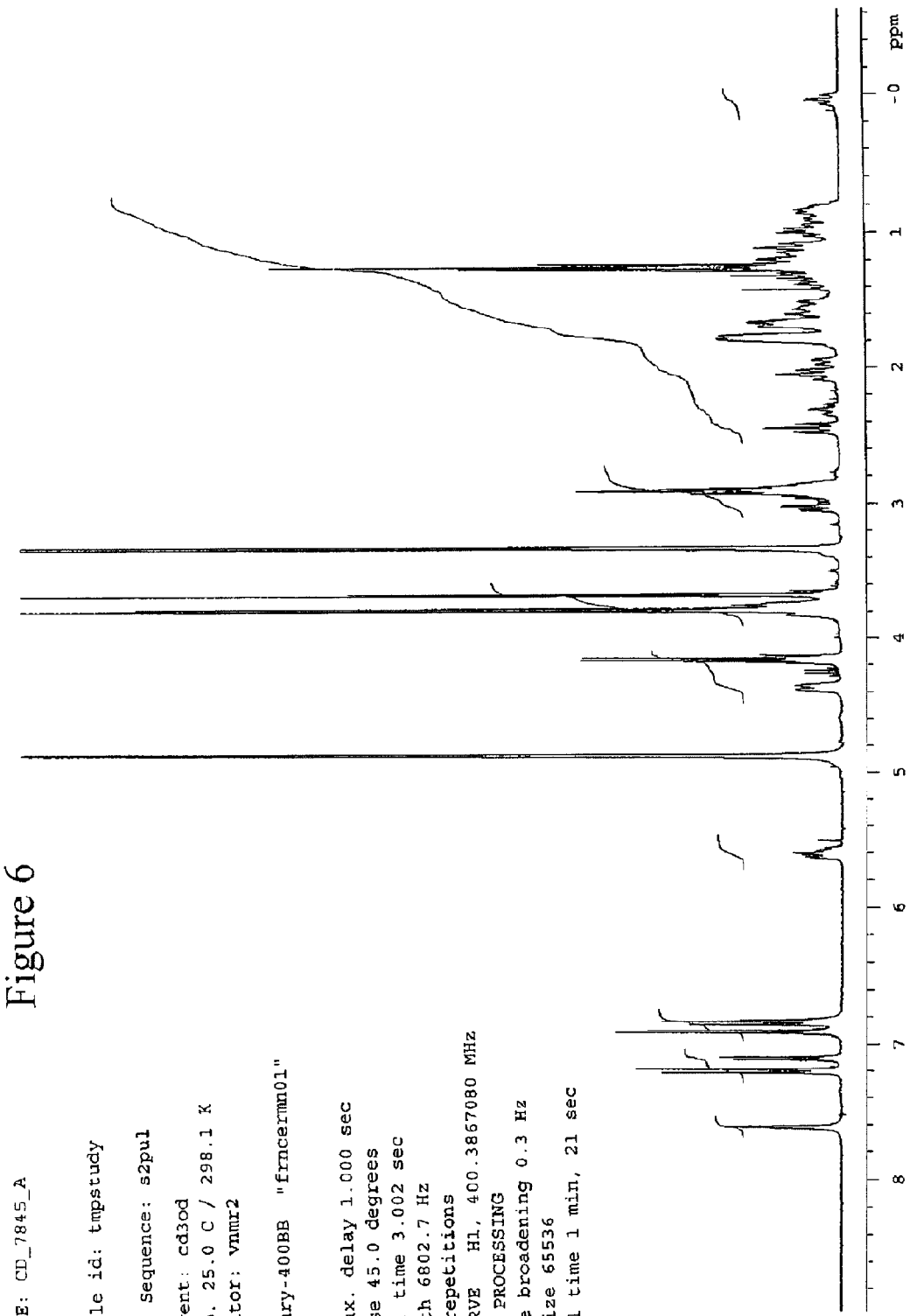
FIG. 6 depicts $^1$H NMR results for the product of Example 8, ethyl 4-cyclohexyl-1-((R)-3-(4-methoxyphenyl)-2-{3-]2-(1-methyl-1 H-imidazol-4-yl)ethyl]thioureido}propionyl)piperidine-4-caroxylate (mixture of conformers).

Ethyl 4-cyclohexyl-1-((R)-3-(4-methoxyphenyl)-2-{3-[2-(1-methyl-1H-imidazol-4-yl)ethyl]thioureido}propionyl)piperidine-4-carboxylate Synthetic route identical to that of Example 7.
$^1$H NMR: results presented in FIG. 6 (mixture of conformers).

EXAMPLE 9

Ethyl 4-cyclohexyl-1-((R)-3-(2,4-dichlorophenyl)-2-{3-[2-(1H-imidazol-4-yl)ethy]ureido}propionyl)piperidine-4-carboxylate Synthetic route identical to that of Example 5.
$^1$H NMR/DMSO 100° C.: 0.90 (m, 3H); 1.07-1.27 (m, 8H); 1.60 (m, 3H); 1.74 (m, 2H); 1.96 (dd, 2H, 2.4 Hz, 11.2 Hz); 2.60 (t, 2H, 7.2 Hz); 2.76 (m, 2H); 2.96 (m, 4H); 3.21 (qua, 2H, 7.2 Hz); 4.12 (qua, 2H, 7.2 Hz); 4.99 (qua, 1H); 5.93 (s, 1H); 6.11 (d, 1H, 4.8 Hz); 6.74 (s, 1H); 7.28 (s, 2H); 7.49 (d, 2H, 11.2 Hz); 7.97 (s, 1H)

EXAMPLE 10

Ethyl 4-cyclohexyl-1-[(R)-2-{3-[5-(1H-imidazol-4-yl)pentyl]-ureido}-3-(4-methoxyphenyl)propionyl] piperidine-4-carboxylate 10-1-1 1-Trityl-1H-imidazole-4-carbaldehyde To a solution containing 1 g (10.4 mmol) of 1H-imidazole-4-carbaldehyde and 3.18 g (11.4 mmol) of trityl chloride suspended in 28 ml of acetonitrile are added dropwise 2.5 ml (17.7 mmol) of triethylamine. After stirring for 2 hours at room temperature, 30 ml of water are added and the crude reaction product is filtered. 3.2 g in the form of a beige-coloured powder are obtained and used in the following step without further purification.

10-1-2 2-[5-(1-Trityl-1H-imidazol-4-yl)pent-4-enyl]isoindole-1,3-dione 0.663 ml (4.43 mmol) of DBU and 1.0 g (2.96 mmol) of 1-trityl-1H-imidazole-4-carbaldehyde are added to 2.41 g (4.43 mmol) of [4-(1,3-dioxo-1,3-dihydroisoindol-2-yl)butyl]triphenylphosphonium bromide. The reaction medium is refluxed for 18 hours. The reaction is stopped by adding aqueous 5% citric acid solution and the organic compounds are extracted with $CH_2Cl_2$. The organic phase is dried over $MgSO_4$, filtered and concentrated. The residue obtained is chromatographed on silica gel (eluent: heptane/EtOAc (6/4)). 785 mg of 2-[5-(1-trityl-1H-imidazol-4-yl)pent-4-enyl]isoindole-1,3-dione are obtained in a yield of 51%.

10-1-3 2-[5-(1-Trityl-1H-imidazol-4-yl)pentyl]isoindole-1,3-dione 785 mg (1.5 mmol) of 2-[5-(1-trityl-1H-imidazol-4-yl)pent-4-enyl]isoindole-1,3-dione, 10 ml of a MeOH/THF mixture (6/4) and 392 mg of 10% Pd/C are introduced into a Parr bomb. The reaction medium is stirred at room temperature under a hydrogen pressure of 5 bar. After 4 hours, the reaction medium is filtered through Celite and concentrated. The crude product obtained is chromatographed on silica gel (eluent: heptane/EtOAc (5/5) and then $CH_2Cl_2$/MeOH (9/1)). 380 mg of 2-[5-(1-trityl-1H-imidazol-4-yl)pentyl]isoindole-1,3-dione in the form of a white powder are obtained in a yield of 48%.

$^1$H NMR CDCl$_3$: 1.30 (pent, 2H, J=6.6 Hz); 1.55-1.64 (m, 4H); 2.45 (t, 2H, J=7.5 Hz); 3.58 (t, 2H, J=7.3 Hz); 6.43 (s, 1H); 7.09 (m, 6H); 7.27 (m, 7H); 7.62 (m, 2H); 7.77 (m, 2H).

10-1-4 5-(1H-imidazol-4-yl)pentylamine bis(trifluoroacetate)

0.10 ml of hydrazine hydrate is added to 380 mg (0.72 mmol) of 2-[5-(1-trityl-1H-imidazol-4-yl)pentyl]isoindole-1,3-dione dissolved in 10 ml of MeOH. The reaction medium is refluxed for 4 hours. After cooling to room temperature, the mixture is filtered and the filtrate concentrated. The crude product obtained is purified by preparative HPLC. 4 ml of dichloromethane and 0.5 ml of trifluoroacetic acid are added to the residue obtained. The reaction medium is stirred at room temperature for 18 hours. The solvents are evaporated off. 14 mg of a powder are obtained, and are used in the next step without further purification.

10-2 Ethyl 4-cyclohexyl-1-[(R)-2-{3-[5-(1H-imidazol-4-yl)pentyl]ureido}-3-(4-methoxy-phenyl)propionyl]piperidine-4-carboxylate 16 μL of diisopropylethylamine and 10 mg (51 μmol) of 4-nitrophenyl chloroformate are added to 25 mg (47 μmol) of 1-{1-[(R)-2-amino-3-(4-methoxyphenyl)propionyl]-4-cyclohexylpiperidin-4-yl}butan-1-one (cf. preparation 4.4) dissolved in 5 ml of DCM. The reaction mixture is stirred for 2 hours at room temperature. The reaction is stopped by adding water and the organic compounds are extracted with DCM. The organic phase is then dried over $MgSO_4$, filtered and concentrated. The oil obtained is dissolved in 5 ml of DMF at 80° C., and 14 mg of 5-(1H-imidazol-4-yl)pentylamine bis(trifluoroacetate) are added. The reaction mixture is stirred at 80° C. for 5 minutes and for 18 hours at room temperature. The organic phase is washed with 1N sodium hydroxide, extracted with dichloromethane and then dried over $MgSO_4$, filtered and concentrated. The crude product obtained is purified by preparative HPLC. 3 mg of ethyl 4-cyclohexyl-1-[(R)-2-{3-[5-(1H-imidazol-4-yl)pentyl]ureido}-3-(4-methoxyphenyl)propionyl]piperidine-4-carboxylate are obtained in a yield of 10%.

Preparative HPLC Method:
Modulo-cart strategy C18 100×21.2 mm, 5 μm column
UV detector: 210-400 nm
Flow rate: 17 ml/min
Solvent A: $H_2O$+0.05 TFA
Solvent B: $CH_3CN$+0.05 TFA
Gradient:

| Time | composition |
| --- | --- |
| 0.0 min | A = 90%, B = 10% |
| 10.0 min | A = 2%, B = 98% |
| 12.0 min | A = 2%, B = 98% |
| 12.1 min | A = 90%, B = 10% |
| 15.0 min | A = 90%, B = 10% |

HPLC/SM:
Gemini C6 Phenyl 150×3 mm, 3 μm column
UV detector: 190-900 nm
Flow rate: 0.5 ml/min
Solvent A: $CH_3CN$+0.02 TFA
Solvent B: $H_2O$+0.02 TFA
Gradient:

| Time | composition |
| --- | --- |
| 0.0 min | A = 10%, B = 90% |
| 20.0 min | A = 90%, B = 10% |
| 30.0 min | A = 90%, B = 10% |

Retention Time: 12.62 min, 91%, M+H: 595.

EXAMPLE 11

Transactivation Test: Melanocortin Receptors

Cells:
The lines HEK293 are transfected with vectors pCRE-Luc and hMC1lR or hMCl4R. The cells are cultured at 37° C. and 5% $CO_2$, in DMEM medium supplemented with 10% foetal calf serum.

Test Principle:
In the presence of an activator (agonist), the melanocortin receptor will activate the cAMP pathway, which, via the vector CRE-Luc, will lead to the synthesis of luciferase. After addition of a lysis buffer containing a luminescent luciferase substrate, the luminescence proportional to the degree of activation or inhibition of receptor may be measured.

Testing the Products:
The products are dissolved at 10 mM in DMSO. They are tested as a response dose at 0.1% of DMSO final. The range comprising 10 points and a zero starts at 10 μM with four-fold dilutions. To test agonists, the products are tested alone. To determine the antagonist behaviour, the products of interest are tested in the presence of 1 nM NDP-MSH (reference agonist). The cells are inoculated at a rate of 5000 cells per well (384-well plate) in serum-free DMEM medium and incubated overnight at 37° C. and 5% $CO_2$.

The products and the reference ligand (NDP-MSH) are added the following day and the plates are reincubated for 6 hours at 37° C. and 5% $CO_2$. After adding the lysis buffer containing luciferin, the plates are read in a Top-Count machine. The results are normalized as percentage of activity using the 100% (cells+NDP-MSH at 10 nM) and 0% (cells alone) controls. An EC50 is calculated for each product using the XLFit software. The results are given in nM and presented in the table below.

| EC50 hMC1-R (nM) | EC50 hMC4-R (nM) |
|---|---|
| 2000 | 60 |
| 1000 | 50 |
| 2000 | 50 |
| 500 | 20 |
| 2000 | 15 |
| 2000 | 10 |
| 1000 | 50 |
| 1000 | 50 |
| 1000 | 2 |
| 250 | 5 |

These results show a selectivity differential of the compounds according to the invention of a factor of 20 or more between the activity on the human MC4 receptor with respect to the human MC1 receptor. It has thus been demonstrated that the compounds of the invention are highly selective for the MC4 receptor.

The invention claimed is:
1. A compound of formula (I):

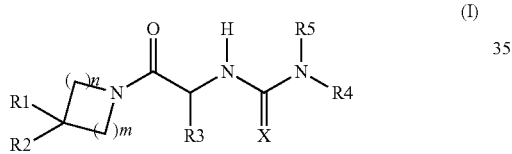

in which:
R1 represents a hydrogen atom, an aryl, a substituted aryl, an alkyl, a cycloalkyl or a cycloalkylalkyl,
R2 represents a hydrogen atom, a hydroxyl or a lower alkyl, a substituted lower alkyl, a higher alkyl, a substituted higher alkyl, a cycloalkyl, a cycloalkylalkyl, a lower alkoxy, a substituted lower alkoxy, a higher alkoxy, a substituted higher alkoxy, a cycloalkylalkoxy, an acyloxy, an acyl, an alkoxycarbonyl, a carboxamide, a carboxylic acid, a cyano or an amino disubstituted with an acyl and an aryl or alkyl,
R3 represents an aralkyl or a substituted aralkyl,
R4 represents a heteroaralkyl or a substituted heteroaralkyl,
R5 represents a hydrogen atom or an alkyl,
X represents an oxygen atom or a sulfur atom,
n, m may be equal to 1 or 2;
or a corresponding salt or enantiomer, having antagonist activity with respect to the MC4R receptor.
2. The compound according to claim 1, having antagonist activity with respect to the MC4R receptor with an EC50 of less than or equal to 60 nM.
3. The compound according to claim 1, wherein the compound is selected from the group consisting of:
tert-Butyl 4-cyclohexyl-1-[2-{3-[2-(1H-imidazol-4-yl) ethyl]ureido}-3-(4-methoxyphenyl)-propionyl]piperidine-4-carboxylamide;
1-[(R)-2-(4-Butyryl-4-cyclohexylpiperidin-1-yl)-1-(4-methoxybenzyl)-2-oxoethyl]-3-[2-(1-methyl-1H-imidazol-4-yl)ethyl]urea;
1-[(R)-2-(4-Butyryl-4-cyclohexylpiperidin-1-yl)-1-(4-methoxybenzyl)-2-oxoethyl]-3-[2-(1H-[1,2,3]triazol-4-yl)ethyl]urea;
Ethyl 4-cyclohexyl-1-[(R)-2-{3-[3-(3H-imidazol-4-yl) propyl]ureido}-3-(4-methoxyphenyl)propionyl]piperidine-4-carboxylate;
Ethyl 4-cyclohexyl-1-((R)-3-(3,4-dichlorophenyl)-2-{3-[2-(1H-imidazol-4-yl)ethyl]ureido}propionyl]piperidine-4-carboxylate;
Ethyl 4-cyclohexyl-1-[(R)-3-(3,4-dichlorophenyl)-2-{3-[2-(3-methyl-3H-imidazol-4-yl)ethyl] ureido}propionyl]piperidine-4-carboxylate;
Ethyl 4-cyclohexyl-1-[(R)-2-{3-[3-(1H-imidazol-4-yl) propyl]thioureido}-3-(4-methoxyphenyl)propionyl]piperidine-4-carboxylate;
Ethyl 4-cyclohexyl-1-((R)-3-(4-methoxyphenyl)-2-{3-[2-(1-methyl-1H-imidazol-4-yl)ethyl] thioureido}propionyl)piperidine-4-carboxylate;
Ethyl 4-cyclohexyl-1-((R)-3-(2,4-dichlorophenyl)-2-{3-[2-(1H-imidazol-4-yl)ethyl]ureido}propionyl)piperidine-4-carboxylate;
Ethyl 4-cyclohexyl-1-[(R)-2-{3-[5-(1H-imidazol-4-yl) pentyl]ureido}-3-(4-methoxyphenyl)propionyl]piperidine-4-carboxylate;
4-Cyclohexyl-1-(3-(4-methoxyphenyl)-2-{3-[(R)-2-(1-methyl-1H-imidazol-4-yl)ethyl]ureido}propionyl)piperidine-4-tert-butylcarbamoyl;
4-Cyclohexyl-1-(3-(4-methoxyphenyl)-2-{3-[(R)-2-(1H-[1,2,3]triazol-4-yl)ethyl]ureido}propionyl)piperidine-4-tert-butylcarbamoyl;
4-Cyclohexyl-1-[(R)-2-{3-[3-(1H-imidazol-4-yl)propyl] ureido}-3-(4-methoxyphenyl)propionyl]piperidine-4-tert-butylcarbamoyl;
4-Cyclohexyl-1-[(R)-2-{3-[5-(1H-imidazol-4-yl)pentyl] ureido}-3-(4-methoxyphenyl)propionyl]piperidine-4-tert-butylcarbamoyl;
4-Cyclohexyl-1-((R)-3-(4-methoxyphenyl)-2-{3-[2-(1-methyl-1H-imidazol-4-yl)ethyl]thioureido}propionyl) piperidine-4-tert-butylcarbamoyl;
4-Cyclohexyl-1-[(R)-2-{3-[3-(1H-imidazol-4-yl)propyl] thioureido}-3-(4-methoxyphenyl)propionyl]piperidine-4-tert-butylcarbamoyl;
1-[(R)-2-(4-Butyryl-4-cyclohexylpiperidin-1-yl)-1-(4-methoxybenzyl)-2-oxoethyl]-3-[2-(1-methyl-1H-imidazol-4-yl)ethyl]thiourea;
1-[(R)-2-(4-Butyryl-4-cyclohexylpiperidin-1-yl)-1-(4-methoxybenzyl)-2-oxoethyl]-3-[2-(1H-[1,2,3]triazol-4-yl)ethyl]thiourea;
Ethyl 4-cyclohexyl-1-((R)-3-(3,4-dichlorophenyl)-2-{3-[2-(1-methyl-1H-imidazol-4-yl)ethyl] ureido}propionyl)piperidine-4-carboxylate;
Ethyl 4-cyclohexyl-1-((R)-3-(3,4-dichlorophenyl)-2-{3-[5-(1H-imidazol-4-yl)pentyl]ureido}propionyl)piperidine-4-carboxylate;
Ethyl 4-cyclohexyl-1-((R)-3-(2,4-dichlorophenyl)-2-{3-[2-(1-methyl-1H-imidazol-4-yl)ethyl] ureido}propionyl)piperidine-4-carboxylate;
Ethyl 4-cyclohexyl-1-((R)-3-(2,4-dichlorophenyl)-2-{3-[2-(3-methyl-3H-imidazol-4-yl)ethyl] ureido}propionyl)piperidine-4-carboxylate;
Ethyl 4-cyclohexyl-1-((R)-3-(2,4-dichlorophenyl)-2-{3-[5-(1H-imidazol-4-yl)pentyl]ureido}propionyl)piperidine-4-carboxylate;

1-[(R)-2-(4-Cyclohexyl-4-propoxypiperidin-1-yl)-1-(4-methoxybenzyl)-2-oxoethyl]-3-[2-(1-methyl-1H-imidazol-4-yl)ethyl]urea;

1-[(R)-2-(4-Cyclohexyl-4-propoxypiperidin-1-yl)-1-(4-methoxybenzyl)-2-oxoethyl]-3-[2-(1H-[1,2,3]triazol-4-yl)ethyl]urea;

1-[(R)-2-(4-Cyclohexyl-4-propoxypiperidin-1-yl)-1-(4-methoxybenzyl)-2-oxoethyl]-3-[3-(1H-imidazol-4-yl)propyl]urea;

1-[(R)-2-(4-Cyclohexyl-4-propoxypiperidin-1-yl)-1-(4-methoxybenzyl)-2-oxoethyl]-3-[5-(1H-imidazol-4-yl)pentyl]urea;

1-[(R)-2-(4-Cyclohexyl-4-propoxypiperidin-1-yl)-1-(4-methoxybenzyl)-2-oxoethyl]-3-[2-(1-methyl-1H-imidazol-4-yl)ethyl]thiourea;

1-[2-(4-Cyclohexyl-4-propoxypiperidin-1-yl)-1-(4-methoxybenzyl)-2-oxoethyl]-3-[3-(1H-imidazol-4-yl)propyl]thiourea;

1-[(R)-2-(4-Butyryl-4-cyclohexylpiperidin-1-yl)-1-(4-chlorobenzyl)-2-oxoethyl]-3-[2-(1-methyl-1H-imidazol-4-yl)ethyl]urea;

1-[(R)-2-(4-Butyryl-4-cyclohexylpiperidin-1-yl)-1-(4-chlorobenzyl)-2-oxoethyl]-3-[2-(1H-[1,2,3]triazol-4-yl)ethyl]urea;

1-[(R)-2-(4-Butyryl-4-cyclohexylpiperidin-1-yl)-1-(4-chlorobenzyl)-2-oxoethyl]-3-[3-(1H-imidazol-4-yl)propyl]urea;

1-[(R)-2-(4-Butyryl-4-cyclohexylpiperidin-1-yl)-1-(4-chlorobenzyl)-2-oxoethyl]-3-[5-(1H-imidazol-4-yl)pentyl]urea;

1-[(R)-2-(4-Butyryl-4-cyclohexylpiperidin-1-yl)-1-(4-chlorobenzyl)-2-oxoethyl]-3-[2-(1-methyl-1H-imidazol-4-yl)ethyl]thiourea;

1-[(R)-2-(4-Butyryl-4-cyclohexylpiperidin-1-yl)-1-(4-chlorobenzyl)-2-oxoethyl]-3-[3-(1H-imidazol-4-yl)propyl]thiourea;

1-[(R)-2-(4-Butyryl-4-cyclohexylpiperidin-1-yl)-1-(2,4-dichlorobenzyl)-2-oxoethyl]-3-(1H-imidazol-4-yl)methyl)urea;

1-[(R)-2-(4-Butyryl-4-cyclohexylpiperidin-1-yl)-1-(4-fluorobenzyl)-2-oxoethyl]-3-[2-(1-methyl-1H-imidazol-4-yl)ethyl]urea;

1-[(R)-2-(4-Butyryl-4-cyclohexylpiperidin-1-yl)-1-(4-fluorobenzyl)-2-oxoethyl]-3-[2-(1H-[1,2,3]triazol-4-yl)ethyl]urea;

1-[(R)-2-(4-Butyryl-4-cyclohexylpiperidin-1-yl)-1-(4-fluorobenzyl)-2-oxoethyl]-3-[3-(1H-imidazol-4-yl)propyl]urea;

1-[(R)-2-(4-Butyryl-4-cyclohexylpiperidin-1-yl)-1-(4-fluorobenzyl)-2-oxoethyl]-3-[5-(1H-imidazol-4-yl)pentyl]urea;

1-[(R)-2-(4-Butyryl-4-cyclohexylpiperidin-1-yl)-1-(4-fluorobenzyl)-2-oxoethyl]-3-[2-(1-methyl-1H-imidazol-4-yl)ethyl]thiourea; and 1-[(R)-2-(4-Butyryl-4-cyclohexylpiperidin-1-yl)-1-(4-fluorobenzyl)-2-oxoethyl]-3-[3-(1H-imidazol-4-yl)propyl]thiourea.

4. A medicament comprising the compound according to claim 1.

5. A pharmaceutical composition comprising a compound according to claim 1 and a pharmaceutically acceptable support.

6. The compound according to claim 1, which is tert-butyl 4-cyclohexyl-1-[2-{3-[2-(1H-imidazol-4-yl)ethyl]ureido}-3-(4-methoxyphenyl)-propionyl]piperidine-4-carboxylamide.

7. The compound according to claim 1, which is 1-[(R)-2-(4-butyryl-4-cyclohexylpiperidin-1-yl)-1-(4-methoxybenzyl)-2-oxoethyl]-3-[2-(1-methyl-1H-imidazol-4-yl)ethyl]urea.

8. The compound according to claim 1, which is 1-[(R)-2-(4-butyryl-4-cyclohexylpiperidin-1-yl)-1-(4-methoxybenzyl)-2-oxoethyl]-3-[2-(1H-[1,2,3]triazol-4-yl)ethyl]urea.

9. The compound according to claim 1, which is ethyl 4-cyclohexyl-1-[(R)-2-{3-[3-(3H-imidazol-4-yl)propyl]ureido}-3-(4-methoxyphenyl)propionyl]piperidine-4-carboxylate.

10. The compound according to claim 1, which is ethyl 4-cyclohexyl-1-((R)-3-(3,4-dichlorophenyl)-2-{3-[2-(1H-imidazol-4-yl)ethyl]ureido}propionyl)piperidine-4-carboxylate.

11. The compound according to claim 1, which is ethyl 4-cyclohexyl-1-((R)-3-(3,4-dichlorophenyl)-2-{3-[2-(3-methyl-3H-imidazol-4-yl)ethyl]ureido}propionyl)piperidine-4-carboxylate.

12. The compound according to claim 1, which is ethyl 4-cyclohexyl-1-[(R)-2-{3-[2-(1H-imidazol-4-yl)propyl]thioureido}-3-(4-methoxyphenyl)propionyl]piperidine-4-carboxylate.

13. The compound according to claim 1, which is ethyl 4-cyclohexyl-1-((R)-3-(4-methoxyphenyl)-2-{3-[2-(1-methyl-1H-imidazol-4-yl)ethyl]thioureido}propionyl)piperidine-4-carboxylate.

14. The compound according to claim 1, which is ethyl 4-cyclohexyl-1-((R)-3-(2,4-dichlorophenyl)-2-{3-[2-(1H-imidazol-4-yl)ethyl]-ureido}propionyl)piperidine-4-carboxylate.

15. The compound according to claim 1, which is ethyl 4-cyclohexyl-1-[(R)-2-{3-[5-(1H-imidazol-4-yl)pentyl]ureido}-3-(4-methoxyphenyl)propionyl]piperidine-4-carboxylate.

16. A method for eliciting an antagonist response to a melanocortin receptor MC4R in a cell, the method comprising contacting said cell with an effective melanocortin receptor MC4R antagonist amount of the compound according to claim 1.

17. A method for eliciting an antagonist response to a melanocortin receptor MC4R in a cell, the method comprising contacting said cell with an effective melanocortin receptor MC4R antagonist amount of the compound according to claim 2.

18. A method for eliciting an antagonist response to a melanocortin receptor MC4R in a cell, the method comprising contacting said cell with an effective melanocortin receptor antagonist amount of the compound which is:

(a) tert-butyl 4-cyclohexyl-1-[2-{3-[2-(1H-imidazol-4-yl)ethyl]ureido}-3-(4-methoxyphenyl)propionyl]piperidine-4-carboxylamide;

(b) 1-[(R)-2-(4-butyryl-4-cyclohexylpiperidin-1-yl)-1-(4-methoxybenzyl)-2-oxoethyl]-3-[2-(1-methyl-1H-imidazol-4-yl)ethyl]urea;

(c) 1-[(R)-2-(4-butyryl-4-cyclohexylpiperidin-1-yl)-1-(4-methoxybenzyl)-2-oxoethyl]-3-[2-(1H-[1,2,3]triazol-4-yl)ethyl]urea;

(d) ethyl 4-cyclohexyl-1-[(R)-2-{3-[3-(3H-imidazol-4-yl)propyl]ureido}-3-(4-methoxyphenyl)propionyl]piperidine-4-carboxylate;

(e) ethyl 4-cyclohexyl-1-((R)-3-(3,4-dichlorophenyl)-2-{3-[2-(1H-imidazol-4-yl)ethyl]ureido}propionyl)piperidine-4-carboxylate;

(f) ethyl 4-cyclohexyl-1-((R)-3-(3,4-dichlorophenyl)-2-{3-[2-(3-methyl-3H-imidazol-4-yl)ethyl]ureido}propionyl)piperidine-4-carboxylate;

(g) ethyl 4-cyclohexyl-1-[(R)-2-{3-[2-(1H-imidazol-4-yl)propyl]thioureido}-3-(4-methoxyphenyl)propionyl]piperidine-4-carboxylate;
(h) ethyl 4-cyclohexyl-1-((R)-3-(4-methoxyphenyl)-2-{3-[2-(1-methyl-1H-imidazol-4-yl)ethyl]thioureido}propionyl)piperidine-4-carboxylate;
(i) ethyl 4-cyclohexyl-1-((R)-3-(2,4-dichlorophenyl)-2-{3-[2-(1H-imidazol-4-yl)ethyl]ureido}propionyl)piperidine-4-carboxylate; or
(j) ethyl 4-cyclohexyl-1-[(R)-2-{3-[5-(1H-imidazol-4-yl)pentyl]ureido}-3-(4-methoxyphenyl)propionyl]piperidine-4-carboxylate.

* * * * *